United States Patent
Boupat et al.

(10) Patent No.: US 7,632,905 B2
(45) Date of Patent: Dec. 15, 2009

(54) BLOCK COPOLYMER, COMPOSITION COMPRISING IT AND COSMETIC TREATMENT PROCESS

(75) Inventors: Nicolas Passade Boupat, Pau (FR); Olivier Guerret, La Tour de Salvagny (FR); Nathalie Mougin, Paris (FR); Xavier Schultze, Pontault-Combault (FR); Franck Hernandez, Villemonble (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/101,648

(22) Filed: Apr. 8, 2005

(65) Prior Publication Data

US 2006/0030685 A1    Feb. 9, 2006

Related U.S. Application Data

(60) Provisional application No. 60/562,255, filed on Apr. 15, 2004.

(30) Foreign Application Priority Data

Apr. 9, 2004    (FR) .................................. 04 50718

(51) Int. Cl.
C08F 118/02    (2006.01)
A61K 6/00    (2006.01)
A61K 7/00    (2006.01)
A61K 31/74    (2006.01)

(52) U.S. Cl. ................... 526/319; 424/70.1; 424/70.11; 424/70.16; 424/78.02; 424/78.03; 526/318

(58) Field of Classification Search ................ 525/256, 525/259, 262; 526/135, 318, 319; 524/556; 424/61, 70.16, 70.1, 70.11, 78.02, 78.03, 424/78.18, 401
See application file for complete search history.

(56) References Cited

U.S. PATENT DOCUMENTS

| | | | |
|---|---|---|---|
| 5,763,548 A * | 6/1998 | Matyjaszewski et al. .... | 526/135 |
| 5,919,871 A | 7/1999 | Nicol et al. | |
| 6,153,705 A | 11/2000 | Corpart et al. | |
| 6,239,226 B1 * | 5/2001 | Fischer et al. .............. | 525/256 |
| 6,255,448 B1 | 7/2001 | Grimaldi et al. | |
| 6,262,179 B1 | 7/2001 | Nicol | |
| 6,262,206 B1 * | 7/2001 | Nesvadba et al. ........... | 526/220 |
| 6,361,768 B1 * | 3/2002 | Galleguillos et al. ..... | 424/70.12 |
| 6,403,106 B1 * | 6/2002 | Sebag et al. ................ | 424/401 |
| 6,437,040 B2 | 8/2002 | Anthony et al. | |
| 6,506,837 B2 | 1/2003 | Destarac et al. | |
| 6,545,098 B1 | 4/2003 | Bouhadir et al. | |
| 6,579,947 B2 | 6/2003 | Heitz et al. | |
| 6,657,043 B1 | 12/2003 | Guerret et al. | |
| 6,805,872 B2 * | 10/2004 | Mougin ..................... | 424/401 |
| 6,812,291 B1 | 11/2004 | Corpart et al. | |
| 6,825,290 B2 | 11/2004 | Adam et al. | |
| 7,309,736 B2 * | 12/2007 | Taniguchi et al. .......... | 525/88 |
| 2002/0115780 A1 * | 8/2002 | Mougin ..................... | 524/556 |
| 2002/0198347 A1 | 12/2002 | Adam et al. | |
| 2003/0162896 A1 | 8/2003 | Destarac et al. | |
| 2004/0071871 A1 | 4/2004 | Queval et al. | |
| 2004/0082494 A1 | 4/2004 | Queval et al. | |
| 2004/0097674 A1 | 5/2004 | Suau et al. | |
| 2004/0122193 A1 | 6/2004 | Wilczewska et al. | |
| 2004/0132961 A1 | 7/2004 | Wilczewska et al. | |
| 2004/0209995 A1 | 10/2004 | Adam et al. | |
| 2005/0131144 A1 | 6/2005 | Adam et al. | |

FOREIGN PATENT DOCUMENTS

| | | |
|---|---|---|
| FR | 2 821 620 | 9/2002 |
| WO | WO 96/24620 | 8/1996 |
| WO | WO 96/30421 | 10/1996 |
| WO | WO 97/18247 | 5/1997 |
| WO | WO 98/01478 | 1/1998 |
| WO | WO 98/58974 | 12/1998 |
| WO | WO 99/03894 | 1/1999 |
| WO | WO 99/31144 | 6/1999 |
| WO | WO 99/35177 | 7/1999 |
| WO | WO 00/71501 | 11/2000 |
| WO | WO 00/71591 | 11/2000 |
| WO | WO 01/16187 | 3/2001 |
| WO | WO 02/28357 | 4/2002 |

(Continued)

OTHER PUBLICATIONS

Benoit et al., "Development of a Universal Alkoxyamine for 'Living' Free Radical Polymerizations," J. Am. Chem. Soc., 1999, 121(16), 3904-3920.

(Continued)

*Primary Examiner*—David Wu
*Assistant Examiner*—Michael M Bernshteyn
(74) *Attorney, Agent, or Firm*—Finnegan, Henderson, Farabow, Garrett & Dunner, L.L.P.

(57) ABSTRACT

The present invention relates to a linear ethylenic block copolymer comprising in each block at least one ionic hydrophilic unit, which may be different from one block to another, the said ionic hydrophilic unit being present in each block in a proportion of from 2% to 100% by weight relative to the weight of the said block.

The invention also relates to a cosmetic or pharmaceutical composition comprising such a copolymer, and also to a cosmetic process for making up or caring for keratin materials using the said composition.

51 Claims, No Drawings

FOREIGN PATENT DOCUMENTS

| WO | WO 02/28358 | 4/2002 |
|----|-------------|--------|
| WO | WO 2004013192 A1 * | 2/2004 |

OTHER PUBLICATIONS

Benoit et al., "Kinetics and Mechanism of Controlled Free-Radical Polymerization of Styrene and *n*-Butyl Acrylate in the Presence of an Acyclic β-Phosphonylated Nitroxide," J. Am. Chem. Soc., 2000, 122(25), 5929-5939.

Chiefari et al., "Living Free-Radical Polymerization by Reversible Addition-Fragmentation Chain Transfer: The RAFT Process," Macromolecules, 1998, 31(16), 5559-5562.

Chong et al., "A more versatile route to block copolymers and other polymers of complex architecture by living radical polymerization: The RAFT process," Macromolecules, 1999, 32(6), 2071-2074.

Fischer, "The Persistent Radical Effect: A Principle for Selective Radical Reactions and Living Radical Polymerizations," Chemical Reviews, 2001, 101(12), 3581-3610.

Hawker, "Living free radical polymerization: A unique technique for preparation of controlled macromolecular architectures," Chem. Res., 1997, 30, 373-382.

Malmstrom et al., "Macromolecular engineering via living free radical polymerizations," Macromol. Chem. Phys., 1998, 199(6), 923-935.

Wang et al., "Controlled/'living' radical polymerization, atom transfer radical polymerization in the presence of transition-metal complexes," J. Am. Chem. Soc., 1995, 117(20), 5614-5615.

* cited by examiner

BLOCK COPOLYMER, COMPOSITION COMPRISING IT AND COSMETIC TREATMENT PROCESS

The present invention relates to novel block copolymers, to their use especially in the cosmetics field and to compositions comprising them.

In the cosmetics field, polymers with conflicting properties are often sought: to obtain good tack-free fixing; good moisture resistance of the products with good removal on shampooing; or a makeup composition that combines comfort of use and staying power. Moreover, these polymers should preferably be conveyed in water, in soluble or dispersible form.

It is for this reason that formulators have turned more particularly toward copolymers, and in particular toward block polymers, which have advantageous mechanical properties. They may especially allow these conflicting properties to be obtained, since they result from the combination, within the same chain, of blocks with different properties: one possibly providing rigidity and the other flexibility, for example.

Thus, the styling properties of styling products or lacquers may be modified. This also makes it possible, in the case of nail varnishes, to optimize the wear resistance and the adhesion of the films to the nail, without generating any tack on the surface of the films. To do this, within the same chain, a block providing adhesion and a block that prevents tack may be combined.

In the cosmetics field, copolymers based on PEO-PPO (polyethylene oxide/polypropylene oxide) are more particularly known as water-conveyable block copolymers. However, these polymers do not have satisfactory mechanical properties. In particular, they do not provide any hairstyle hold.

Among the other water-conveyable block copolymers that may be mentioned are those described in patent application WO 02/28358. Block copolymers of which one block is a copolymer predominantly comprising nonionic hydrophilic units mixed with hydrophobic units are described in particular. These copolymers have a nonionic nature. To make them water-soluble, the amount of hydrophilic unit is very high; this limitation does not allow access to a wide range of structures. This document also describes block polymers in which one block is a copolymer comprising acrylic acid units, and another block is a nonionic hydrophilic block. However, these block polymers show high fluctuation of their properties as a function of the humidity.

This is likewise the case for the block copolymers described in WO 02/28357, which are water-soluble, and in which all the blocks are formed from nonionic monomers, but which also have high fluctuations of their properties as a function of the humidity.

Mention may also be made of patent application WO 00/71591, which describes block copolymers comprising a cationic homopolymer block combined with a nonionic hydrophilic block, and the use of these copolymers to improve the foam quality in body hygiene products.

However, these polymers have the drawback of being sparingly compatible with the anionic compounds, especially the anionic surfactants, generally used in shampoos. Moreover, when they are used in styling products, for example of lacquer type, these polymers have the defect of being difficult to remove by shampooing.

Diblock or triblock copolymers that can give gelled aqueous compositions are also known from patent application WO 01/16187; these copolymers may especially be of the poly (styrene/methacrylic acid)-b-poly(ethyl acrylate/methacrylic acid) type. However, these copolymers are thickeners, which, in certain cases, may be considered as a drawback, especially by making the formulation difficult. The reason for this is that it is not always desired to obtain gels: this is the case, for example, for aerosols or nail varnishes, for which fluid solutions are necessary.

It has thus been found that the majority of the block copolymers intended to be conveyed in water predominantly comprise hydrophobic units and have a tendency to form gels, which is a drawback.

The aim of the present invention is to propose block copolymers that have advantageous mechanical properties and that may be used in large amount without having a substantial influence on the thickening or gelation, and thus on the viscosity, of the composition containing them. In particular, the copolymers according to the invention do not form a viscoelastic gel in water, i.e. a gel having a modulus of elasticity ($G'$) greater than the modulus of viscosity ($G''$).

Moreover, copolymers forming a film or a deposit that can be removed fully by shampooing are also sought.

One subject of the invention is thus a linear ethylenic block copolymer comprising at least one first block, and at least one second block, each block comprising at least one ionic hydrophilic unit, which may be different from one block to another, the said ionic hydrophilic unit being present in each block in a proportion of from 2% to 100% by weight relative to the weight of the said block.

Another subject is a cosmetic or pharmaceutical composition comprising, in a physiologically acceptable medium, especially a cosmetically or dermatologically acceptable medium, at least one copolymer as defined below.

The copolymers according to the invention have satisfactory mechanical properties: they may be rigid while at the same time having a certain level of flexibility or elasticity, which gives the hair long-lasting hold. They may also show good adhesion without having a tacky feel.

They find a most particular application in the cosmetics field, especially in haircare or in makeup.

When they are used in nail varnishes, these polymers form a deposit that adheres satisfactorily to the nail without, however, being easily worn away.

The block polymer according to the invention is a linear block ethylenic polymer, which is advantageously film-forming.

The term "ethylenic" polymer means a polymer obtained by polymerization of ethylenically unsaturated monomers.

The term "block polymer" means a polymer comprising at least 2 different successive blocks, i.e. blocks of different chemical nature.

The polymer according to the invention is a polymer of linear structure. In contrast, a polymer of nonlinear structure is, for example, a polymer of branched, star or grafted structure, or the like. In particular, all the monomers used to prepare a linear polymer are monofunctional, i.e. they contain only one polymerizable function. The polymerization initiators may themselves be monofunctional or difunctional.

The term "film-forming polymer" means a polymer that is capable by itself or in the presence of an auxiliary film-forming agent of forming a continuous film that adheres to a support, especially to keratin materials.

Each block of the polymer according to the invention is derived from one type of monomer or from several different types of monomer. This means that each block may consist of a homopolymer or a copolymer; this copolymer constituting the block may in turn be a statistical or alternating or gradient copolymer; the distribution of the monomers within each block may thus be random or controlled depending on the nature and/or the reactivity of the monomers and/or the preparation process used.

The block polymer according to the invention thus comprises at least two block, advantageously two blocks (diblock) or three blocks (triblock), each of the blocks comprising at least one ionic hydrophilic monomer, which is present in each block in a proportion of at least 2% by weight relative to the weight of the block.

In each block, the said ionic hydrophilic monomer may in fact be a mixture of different ionic hydrophilic monomers.

Moreover, the ionic hydrophilic monomer(s) may be totally or partially identical, or different, from one block to another.

The ionic hydrophilic monomers are present in each block in a proportion of from 2% to 100% by weight, especially from 3% to 70% by weight, better still from 5% to 50% by weight or even from 8% to 30% by weight, relative to the weight of the block.

A monomer is said to be hydrophilic if the corresponding homopolymer is hydrophilic, i.e. if it is water-soluble or water-dispersible.

The homopolymer is water-soluble if it is soluble in water to a proportion of at least 5% by weight, at 25° C.

The homopolymer is water-dispersible if it forms in water, at a concentration of 5% by weight, at 25° C., a stable suspension or dispersion of fine, generally spherical particles. The mean size of the particles constituting the said dispersion is less than 1 µm and more generally ranges between 5 and 400 nm and preferably from 10 to 250 nm. These particle sizes are measured by light scattering (using a machine of Coulter Counter type).

The hydrophilicity of a monomer may also be defined by the value of the logarithm of the 1-octanol/water apparent partition coefficient, also known as log P; it may be considered that a monomer is hydrophilic when this value is less than or equal to 2, for example between −8 and 2, preferably less than or equal to 1.5, especially less than or equal to 1 and in particular between −7 and 1, or even between −6 and 0.

The log P values are known and are determined according to a standard test that determines the concentration of the monomer in octanol and water.

The values may be calculated especially using the ACD (Advanced Chemistry Development) software solaris V4.67; they may also be obtained from Exploring QSAR: hydrophobic, electronic and steric constants (ACS professional reference book, 1995).

There is also a website that provides estimated values (address: http://esc.syrres.com/interkow/kowdemo.htm).

As mentioned above, the final polymer comprises in each of its blocks at least one hydrophilic monomer present in a proportion of at least 2% by weight relative to the weight of the block.

To do this, it is possible to use as starting monomer ionic hydrophilic monomers as described below, which will be copolymerized according to the prior art so as to obtain the desired polymer.

However, it is also possible to modify the presynthesized polymer, so as to obtain the said hydrophilic monomers.

For example, it is possible to hydrolyze the polymer when it comprises units of (meth)acrylic ester type, which can be hydrolyzed to give units containing a carboxylic acid function; this may be the case when the polymer comprises units of the methyl, ethyl, hydroxyethyl, tert-butyl, benzyl, trimethoxysilyl or ethyltrimethoxysilyl (meth)acrylate type.

The hydrolysis may thus be performed once the polymer has been synthesized, under acidic conditions (for example in the presence of sulfuric acid, hydrochloric acid or trifluoroacetic acid) or basic conditions (for example in the presence of alkaline-earth metal hydroxides such as sodium hydroxide or potassium hydroxide, alkali metal alkoxides such as potassium t-butoxide, or amines such as aqueous ammonia). The hydrolysis generally takes place between 5 and 100° C. and preferably between 15 and 80° C. The hydrolyzed polymer may then be purified by repeated precipitations.

It may also be envisaged to react a compound of the type HO—R—X, NHR'—R—X, HO—R—Y or NHR'—R—Y type (X and Y having the meanings given below) with an already-formed polymer comprising units of the glycidyl or azlactone type.

The ionic hydrophilic monomers present in the final polymer may be chosen from anionic, cationic and/or amphoteric hydrophilic monomers.

Preferably, each of the blocks comprises at least one anionic hydrophilic monomer and/or at least one cationic hydrophilic monomer.

In one particular embodiment, at least one block may comprise both at least one cationic hydrophilic monomer and at least one anionic hydrophilic monomer.

Among the anionic hydrophilic monomers that may especially be mentioned are ethylenically unsaturated monomers comprising, for example, at least one carboxylic acid (COOH), phosphonic acid ($PO_3H_2$) or sulfonic acid ($SO_3H$) function, for instance those of formula (I) below:

(I)

in which:
R1 is a hydrogen atom or a linear or branched hydrocarbon-based radical of the type $C_pH_{2p+1}$, with p being an integer between 1 and 12 inclusive.

R1 may especially represent a methyl, ethyl, propyl or butyl radical. R1 preferably represents hydrogen or a methyl radical.

Z is a divalent group chosen from —COO—, —CONH—, —CONCH$_3$—, —OCO— or —O—; preferably, Z is chosen from —COO— and —CONH—;

x is 0 or 1, preferably 1;

m is 0 or 1;

R2 is a linear, branched or cyclic, optionally aromatic, saturated or unsaturated divalent carbon-based radical of 1 to 30 carbon atoms, which may comprise 1 to 30 hetero atoms chosen from O, N, S and P.

In the radical R2, the hetero atom(s), when it is (they are) present, may be intercalated in the chain of the said radical R2, or alternatively the said radical R2 may be substituted with one or more groups comprising them such as hydroxyl or amino (NH2, NHR' or NR'R" with R' and R", which may be identical or different, representing a linear or branched C1-C22 alkyl, especially methyl or ethyl).

R2 may especially be:
an alkylene radical such as methylene, ethylene, propylene, n-butylene, isobutylene, tert-butylene, n-hexylene, n-octylene, n-dodecylene, n-octadecylene, n-tetradecylene or n-docosanylene;

a phenylene radical —$C_6H_4$-(ortho, meta or para), which is optionally substituted, with a C1-C12 alkyl radical optionally comprising 1 to 8 hetero atoms chosen from O, N, S, and P; or alternatively a benzylene radical —C$_6$H$_4$—CH$_2$—, which is optionally substituted, with a C1-C12 alkyl radical optionally comprising 1 to 8 hetero atoms chosen from O, N, S and P;

a radical of formula —CH$_2$—CHOH—, —CH$_2$—CH$_2$—CHOH—, —CH$_2$—CH$_2$—CH(NH$_2$)—, —CH$_2$—CH(NH$_2$)—, —CH$_2$—CH$_2$—CH(NHR')—, —CH$_2$—CH(NHR')—, —CH$_2$—CH$_2$—CH(NR'R")—, —CH$_2$—CH(NR'R")—, —CH$_2$—CH═CH— with R' and R" representing a linear or branched C1-C18 alkyl, especially methyl or ethyl.

Y is a group chosen from —COOH, —SO$_3$H, —OSO$_3$H, —PO(OH)$_2$ and —OPO(OH)$_2$—.

Among the anionic hydrophilic monomers that are more particularly preferred, mention may be made especially of acrylic acid, methacrylic acid, crotonic acid, itaconic acid, fumaric acid, maleic acid, diacrylic acid, dimethylfumaric acid, citraconic acid, acrylamidopropanesulfonic acid, 2-acrylamido-2-methylpropanesulfonic acid, styrenesulfonic acid, vinylbenzoic acid, vinylphosphoric acid, vinylsulfonic acid, vinylbenzenesulfonic acid, acrylamidoglycolic acid of formula CH2═CH—CONHCH(OH)COOH, vinylphosphonic acid; 2-carboxyethyl(meth)acrylate, sulfopropyl methacrylate or acrylate (CH$_2$═C(CH$_3$)CO$_2$(CH$_2$)$_3$SO$_3$H), sulfoethyl methacrylate or acrylate and vinyl methyl sulfone, 2-(methacryloyloxy)ethyl phosphate of formula CH$_2$═C(CH$_3$)COOC$_2$H$_4$OP(O)(OH)$_2$; diallyl maleate of formula C$_3$H$_5$—CO$_2$—CH═CH—CO$_2$—C$_3$H$_5$; carboxylic anhydrides bearing a vinyl bond, such as maleic anhydride, and also the salts thereof; and mixtures thereof.

The neutralization of the anionic groups may be performed with a mineral base, such as LiOH, NaOH, KOH, Ca(OH)$_2$, NH$_4$OH or Zn(OH)$_2$; or with an organic base such as a primary, secondary or tertiary alkylamine, especially triethylamine or butylamine. This primary, secondary or tertiary alkylamine may comprise one or more nitrogen and/or oxygen atoms and may thus comprise, for example, one or more alcohol functions; mention may be made especially of 2-amino-2-methylpropanol, triethanolamine and 2-dimethylaminopropanol. Mention may also be made of lysine or 3-(dimethylamino)propylamine.

Among the cationic hydrophilic monomers that may be mentioned are ethylenically unsaturated monomers comprising at least one primary, secondary or tertiary amine function, especially those of formula (II) below:

(II)

in which:

R1, Z, x, R2 and m have the same meanings as in formula (I) above;

X is (a) a group of formula —N—R$_6$R$_7$ with R6 and R7 representing, independently of each other, (i) a hydrogen atom, (ii) a linear, branched or cyclic, saturated or unsaturated, optionally aromatic alkyl group containing from 1 to 30 carbon atoms, which may comprise 1 to 10 hetero atoms chosen from O, N, S and P; especially a methyl, ethyl, propyl, isopropyl, n-butyl, t-butyl, isobutyl, lauryl or stearyl group;

(iii) an alkylene oxide group of formula —(R8O)$_y$R9 with R8 representing a linear or branched C2-C4 alkyl, R9 is hydrogen or a linear or branched C1-C30 alkyl radical and y is between 1 and 250 inclusive;

(iv) R6 and R7 may form with the nitrogen atom a saturated or unsaturated optionally aromatic ring containing in total 5, 6, 7 or 8 atoms, and especially 4, 5 or 6 carbon atoms and/or 2 to 4 hetero atoms chosen from O, S and N; the said ring also possibly being fused with one or more other saturated or unsaturated, optionally aromatic rings, each comprising 5, 6 or 7 atoms, and especially 4, 5, 6 or 7 carbon atoms and/or 2 to 4 hetero atoms chosen from O, S and N;

or alternatively X represents (b) a group —R'6-N—R'7- in which R'6 and R'7 form with the nitrogen atom a saturated or unsaturated, optionally aromatic ring, comprising in total 5, 6, 7 or 8 atoms, and especially 4, 5 or 6 carbon atoms and/or 2 to 4 hetero atoms chosen from O, S and N; the said ring possibly being fused with one or more other saturated or unsaturated, optionally aromatic rings, each comprising 5, 6 or 7 atoms, and especially 4, 5, 6, 7. or 8 carbon atoms and/or 2 to 4 hetero atoms chosen from O, S and N.

For example, X may constitute an aromatic or non-aromatic ring comprising a cationizable tertiary amine group or may represent an aromatic or non-aromatic heterocycle containing a cationizable tertiary nitrogen.

Among the preferred radicals X that may be mentioned are radicals of pyridine, indolyl, isoindolinyl, imidazolyl, imidazolinyl, piperidinyl, pyrazolinyl, pyrazolyl, quinoline, pyrazolinyl, pyridinyl, piperazinyl, pyrrolidinyl, quinidinyl, thiazolinyl, morpholine, guanidino or amidino type, and mixtures thereof.

Among the preferred cationic hydrophilic monomers that may be mentioned, alone or as a mixture, are:

2-vinylpyridine, 4-vinylpyridine, allylamine and allylpyridine;

aminoalkyl (meth)acrylates, such as [N,N-di-(C1-C4)alkylamino](C1-C6)alkyl(meth)acrylates or [N-(C1-C4)alkylamino](C1-C6)alkyl(meth)acrylates and especially N,N-dimethylaminoethyl(meth)acrylate, N,N-diethylaminoethyl(meth)acrylate, 2-aminoethyl (meth)acrylate and 2-(N-tert-butylamino)ethyl (meth)acrylate;

aminoalkyl(meth)acrylamides, such as [N,N-di-(C1-C4)alkylamino](C1-C6)alkyl (meth)acrylamides or [N-(C1-C4)alkylamino](C1-C6)alkyl(meth)acrylamides, and especially N,N-dimethylaminopropyl(meth)acrylamide, N,N-dimethylaminoethyl(meth)acrylamide; 3-aminopropyl(meth)acrylamide;

vinylamine, vinylimidazole and 2-(diethylamino)ethylstyrene;

N-vinylimidazole, N-vinyl-2-methylimidazole, N-vinylcarbazole;

and also the salts thereof and/or the quaternized forms thereof.

Among the salified forms that may be mentioned are the salts of mineral acids, such as sulfuric acid, hydrochloric acid, hydrobromic acid, hydriodic acid, phosphoric acid or boric acid.

Mention may also be made of the salts of organic acids, which may comprise one or more carboxylic, sulfonic or phosphonic acid groups. These may be linear, branched or cyclic aliphatic acids or alternatively aromatic acids. These acids may also comprise one or more hetero atoms chosen from O and N, for example in the form of hydroxyl groups. Mention may be made especially of propionic acid, acetic acid, terephthalic acid, citric acid and tartric acid.

The neutralization of the anionic or cationic units, and similarly the quaternization, may be total or partial.

The tertiary amine groups may be quaternized with compounds containing labile halogen, especially alkyl halides such as C1-C12 alkyl chlorides or bromides, for example methyl bromide or ethyl chloride.

These groups may also be quaternized with compounds containing labile halogen comprising carboxylic or sulfonic acid functions, especially sodium chloroacetate; or with cyclic sulfones, for example propane sulfone. Amphoteric hydrophilic monomers (or betaines, containing at least one (+) charge and at least one (−) charge borne by the same monomer) are thus obtained.

The quaternization may be performed on the already-synthesized polymer or on the starting monomers, before polymerization.

The resulting polymers may thus comprise amphoteric monomers possibly corresponding to formula (III)

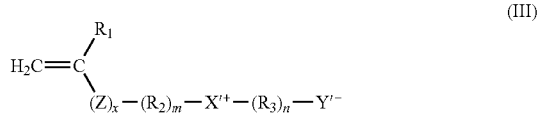

(III)

in which
R1, Z, x, R2 and m have the same meanings as in formula (I) above;
$X'^+$ is a divalent group of formula $-N^+R'_6R'_7$ with R'6 and R'7 representing, independently of each other:
(i) a hydrogen atom,
(ii) a linear, branched or cyclic, optionally aromatic alkyl group, containing from 1 to 30 carbon atoms, which may comprise 1 to 8 hetero atoms chosen from O, N, S and P; for example methyl, ethyl, propyl, isopropyl, n-butyl, t-butyl or isobutyl;
(iii) an alkylene oxide group of formula $-(R8O)_yR9$ with R8 representing a linear or branched C2-C4 alkyl, R9 is hydrogen or a linear or branched C1-C30 alkyl radical and y is between 1 and 250 inclusive;
(iv) R'6 and R'7 may form with the nitrogen atom a saturated or unsaturated, optionally aromatic ring (NR'6R'7 or R'6NR'7), comprising in total 5, 6, 7 or 8 atoms, and especially 4, 5, 6 or 7 carbon atoms and/or 2 to 4 hetero atoms chosen from O, S and N; the said ring possibly being fused with one or more other saturated or unsaturated, optionally aromatic rings, each comprising 5, 6, 7 or 8 atoms, and especially 4, 5, 6 or 7 carbon atoms and/or 2 to 4 hetero atoms chosen from O, S and N;
$Y'^-$ is a group chosen from $-COO^-$, $-SO_3^-$, $-OSO_3^-$, $-PO_3^{2-}$ and $-PO_4^{2-}$;
R3 is a saturated or unsaturated, optionally aromatic, linear, branched or cyclic divalent carbon-based radical of 1 to 30 carbon atoms, which may comprise 1 to 18 hetero atoms chosen from O, N, S and P.

In the radical R3, the hetero atom(s), when it is (they are) present, may be intercalated in the chain of the said radical R3, or alternatively the said radical R3 may be substituted with one or more groups comprising them such as hydroxyl or amino; R3 may especially be:
an alkylene radical such as methylene, ethylene, propylene, n-butylene, isobutylene, tert-butylene, n-hexylene, n-octylene, n-dodecylene, n-octadecylene, n-tetradecylene, n-docosanylene;
a phenylene radical $-C_6H_4-$ (ortho, meta or para), which is optionally substituted, with a C1-C12 alkyl radical optionally comprising 1 to 5 hetero atoms chosen from O, N, S, F, Si and P; or alternatively a benzylene radical $-C_6H_4-CH_2-$, which is optionally substituted, with a C1-C12 alkyl radical optionally comprising 1 to 5 hetero atoms chosen from O, N, S and P;
n is 0 or 1.

Mention may be made in particular of N,N-dimethyl-N-(2-methacryloyloxyethyl)-N-(3-sulfopropyl) ammonium betaine, N,N-dimethyl-N-(3-methacrylamidopropyl)-N-(3-sulfopropyl)ammonium betaine and 1-(3-sulfopropyl)-2-vinylpyridinium betaine, and mixtures thereof.

In one preferred embodiment, the copolymer according to the invention comprises from 4% to 100% by weight, especially from 8% to 80% by weight or even from 10% to 30% by weight, relative to the total weight of the copolymer, of ionic hydrophilic units.

Advantageously, the copolymer according to the invention is soluble or dispersible in water at 25° C., to a proportion of 5% by weight.

Besides the ionic hydrophilic monomers, the blocks of the block copolymer according to the invention may comprise one or more additional monomers chosen from nonionic hydrophilic monomers and hydrophobic monomers, and mixtures thereof.

These additional monomers may be identical or different from one block to another.

This or these additional monomer(s) is (are) ethylenic monomers that are copolymerizable with the ionic hydrophilic monomer(s), irrespective of their coefficient of reactivity.

Preferably, the nonionic hydrophilic monomers may be present in a proportion of from 0 to 98% by weight, especially from 2% to 95% by weight and better still from 3% to 92% by weight, relative to the weight of the block, in at least one block, or even in each block.

Preferably, the hydrophobic monomers may be present in a proportion of from 0 to 98% by weight, especially from 2% to 95% by weight and better still from 3% to 92% by weight, relative to the weight of the block, in at least one block, or even in each block.

Among the nonionic hydrophilic or hydrophobic monomers that may be copolymerized with the ionic hydrophilic monomers to form the polymers according to the invention, mention may be made, alone or as a mixture, of:
(i) ethylenic hydrocarbons containing 2 to 10 carbons, such as ethylene, isoprene or butadiene;
(ii) the (meth)acrylates or formula:

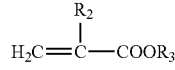

in which $R_2$ is hydrogen or methyl ($CH_3$)
and $R_3$ represents:
a linear or branched alkyl group of 1 to 30 carbon atoms, in which is (are) optionally intercalated one or more hetero atoms chosen from O, N, S and P; the said alkyl group also possibly being optionally substituted with one or more substituents chosen from OH, halogen atoms (Cl, Br, I and F), and groups $-Si(R_4R_5R_6)$ and $-Si(R_4R_5)$ O, in which $R_4$, $R_5$ and $R_6$, which may be identical or different, represent a hydrogen atom, a $C_1$ to $C_6$ alkyl group or a phenyl group; $R_3$ may especially be a methyl, ethyl, propyl, n-butyl, isobutyl, tert-butyl, hexyl, ethylhexyl especially 2-ethylhexyl, octyl, lauryl, isooctyl, isodecyl, dodecyl, cyclohexyl, t-butylcyclohexyl or stearyl group; 2-ethylperfluorohexyl or 2-ethylperfluorooctyl; or a C1-C4 hydroxyalkyl group such as 2-hydroxyethyl, 2-hydroxybutyl and 2-hydroxypropyl; or a $(C_{1-4})$alkoxy-$(C_{1-4})$alkyl group such as methoxyethyl, ethoxyethyl and methoxypropyl, a $C_3$ to $C_{12}$ cycloalkyl group, such as an isobornyl group, a $C_3$ to $C_{20}$ aryl group such as a phenyl group, a C4-C30 aralkyl group ($C_1$ to $C_8$ alkyl group) such as 2-phenylethyl, t-butylbenzyl or benzyl, a 4- to 12-membered heterocyclic group containing one or more hetero atoms chosen from O, N and S, the ring being aromatic or non-aromatic, a heterocycloalkyl (alkyl of 1 to 4 C) group such as furfurylmethyl or tetrahydrofurfurylmethyl, the said cycloalkyl, aryl, aralkyl, heterocyclic or heterocycloalkyl groups possibly being substituted with one or more substituents chosen from hydroxyl groups, halogen atoms and linear or branched C1-4 alkyl groups in which is (are) optionally intercalated one or more hetero atoms chosen from O, N, S and P, the said alkyl groups also possibly being optionally substituted with one or more substituents chosen from —OH, halogen atoms (Cl, Br, I and F), and groups —$Si(R_4R_5R_6)$ and —$Si(R_4R_5)O$, in which $R_4$, $R_5$ and $R_6$, which may be identical or different, represent a hydrogen atom, a $C_1$ to $C_6$ alkyl group or a phenyl group, a group —$(OC_2H_4)_m$—OR", with m=5 to 300 and R"=H or $C_1$ to $C_{30}$ alkyl, for example —$(OC_2H_4)_m$—OH, —$(OC_2H_4)_m$—O-methyl or —$(OC_2H_4)_m$—O-behenyl; a group —$(OC_3H_6)_m$—OR", with m=5 to 300 and R"=H or $C_1$ to $C_{30}$ alkyl, for example —$(OC_3H_6)_m$—OH; or alternatively a random or block mixture of groups $(OC_2H_4)_m$ and $(OC_3H_6)_m$.

(iii) the (meth)acrylamides of formula:

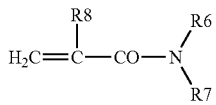

in which $R_8$ denotes H or methyl;

and $R_7$ and $R_6$, which may be identical or different, represent:

a hydrogen atom; or a linear or branched alkyl group of 1 to 30 carbon atoms, in which is (are) optionally intercalated one or more hetero atoms chosen from O, N, S and P; the said alkyl group also possibly being optionally substituted with one or more substituents chosen from —OH, halogen atoms (Cl, Br, I and F), and groups —$Si(R_4R_5R_6)$ and —$Si(R_4R_5)O$, in which $R_4$, $R_5$ and $R_6$ represent a hydrogen atom, a $C_1$ to $C_6$ alkyl group or a phenyl group; $R_6$ or $R_7$ may especially be a methyl, ethyl, propyl, n-butyl, isobutyl, tert-butyl, hexyl, ethylhexyl, octyl, lauryl, isooctyl, isodecyl, dodecyl, cyclohexyl, t-butylcyclohexyl or stearyl group; 2-ethylperfluorohexyl, 2-ethylperfluorooctyl; or a $C_{1-4}$ hydroxyalkyl group such as 2-hydroxyethyl, 2-hydroxybutyl or 2-hydroxypropyl; or a $(C_{1-4})$alkoxy$(C_{1-4})$alkyl group such as methoxyethyl, ethoxyethyl or methoxypropyl, a $C_3$ to $C_{12}$ cycloalkyl group, such as an isobornyl group, a $C_3$ to $C_{20}$ aryl group such as a phenyl group, a $C_4$ to $C_{30}$ aralkyl group ($C_1$ to $C_8$ alkyl group) such as 2-phenylethyl, t-butylbenzyl or benzyl, a 4- to 12-membered heterocyclic group containing one or more hetero atoms chosen from O, N and S, the ring being aromatic or non-aromatic, a heterocycloalkyl group (C1-C4 alkyl), such as furfurylmethyl or tetrahydrofurfurylmethyl, the said cycloalkyl, aryl, aralkyl, heterocyclic or heterocycloalkyl groups possibly being optionally substituted with one or more substituents chosen from hydroxyl groups, halogen atoms and linear or branched C1-C4 alkyl groups in which is (are) optionally intercalated one or more hetero atoms chosen from O, N, S and P, the said alkyl groups also possibly being optionally substituted with one or more substituents chosen from —OH, halogen atoms (Cl, Br, I and F) and groups —$Si(R_4R_5R_6)$ and —$Si(R_4R_5)O$, in which $R_4$, $R_5$ and $R_6$, which may be identical or different, represent a hydrogen atom, a $C_1$ to $C_6$ alkyl group or a phenyl group;

a group —$(OC_2H_4)_m$—OR", with m=5 to 300 and R"=H or $C_1$ to $C_{30}$ alkyl, for example —$(OC_2H_4)_m$—OH, —$(OC_2H_4)_m$—O-methyl or —$(OC_2H_4)_m$—O-behenyl; a group —$(OC_3H_6)_m$—OR", with m=5 to 300 and R"=H or $C_1$ to $C_{30}$ alkyl, for example —$(OC_3H_6)_m$—OH; or alternatively a random or block mixture of groups $(OC_2H_4)_m$ and $(OC_3H_6)_m$.

Examples of such additional monomers are (meth)acrylamide, N-ethyl(meth)acrylamide, N-butylacrylamide, N-t-butylacrylamide, N-isopropylacrylamide, N,N-dimethyl(meth)acrylamide, N,N-dibutylacrylamide, N-octylacrylamide, N-dodecylacrylamide, N-undecylacrylamide and N-(2-hydroxypropylmethacrylamide).

(iv) the vinyl compounds of formula:

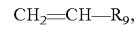

$CH_2=CH-R_9$, in which $R_9$ is a hydroxyl group; a halogen (Cl or F); an $NH_2$ group; an $OR_{10}$ group in which $R_{10}$ represents a phenyl group or a $C_1$ to $C_{12}$ alkyl group (the monomer is a vinyl or allylic ether); an acetamide group (NH-$COCH_3$); a group $OCOR_{11}$ in which $R_{11}$ represents a linear or branched alkyl group of 2 to 12 carbons (the monomer is a vinyl or allylic ester), C3-C12 cycloalkyl, C3-C20 aryl or C4-C30 arallyl; or alternatively $R_9$ is chosen from:

a linear or branched alkyl group containing 1 to 30 carbon atoms, in which is (are) optionally intercalated one or more hetero atoms chosen from O, N, S and P; the said alkyl group also possibly being optionally substituted with one or more substituents chosen from —OH, halogen atoms (Cl, Br, I and F) and groups —$Si(R_4R_5R_6)$ and —$Si(R_4R_5)O$, in which $R_4$, $R_5$ and $R_6$, which may be identical or different, represent a hydrogen atom, a $C_1$ to $C_6$ alkyl group or a phenyl group;

a $C_3$ to $C_{12}$ cycloalkyl group such as isobornyl or cyclohexane, a $C_3$ to $C_{20}$ aryl group such as phenyl, a $C_4$ to $C_{30}$ arylalkyl or alkylaryl group ($C_1$ to $C_8$ alkyl group) such as 2-phenylethyl or benzyl, a 4- to 12-membered heterocyclic group containing one or more hetero atoms chosen from O, N and S, the ring being aromatic or non-aromatic, such as N-vinylpyrrolidone and N-vinylcaprolactam;

a heterocycloalkyl group (alkyl of 1 to 4 C), such as furfurylmethyl or tetrahydrofurfurylmethyl, the said cycloalkyl, aryl, aralkyl, heterocyclic or heterocycloalkyl groups possibly being optionally substituted with one or more substituents chosen from hydroxyl groups, halogen atoms and linear or branched alkyl groups of 1 to 4 C in which is (are) optionally intercalated one or more hetero atoms chosen from O, N, S and P, the said alkyl groups also possibly being optionally substituted with one or more substituents chosen from —OH, halogen atoms (Cl, Br, I and F) and groups —Si(R$_4$R$_5$R$_6$) and —Si(R$_4$R$_5$)O, in which R$_4$, R$_5$ and R$_6$, which may be identical or different, represent a hydrogen atom, a C$_1$ to C$_6$ alkyl group or a phenyl group.

Examples of such additional monomers are vinylcyclohexane and styrene (hydrophobic); N-vinylpyrrolidone and N-vinylcaprolactam (nonionic hydrophilic); vinyl acetate, vinyl propionate, vinyl butyrate, vinyl ethylhexanoate, vinyl neononanoate and vinyl neododecanoate (hydrophobic); methyl vinyl ether, ethyl vinyl ether and isobutyl vinyl ether;

(v) the allylic compounds of formula:

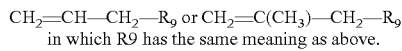
CH$_2$=CH—CH$_2$—R$_9$ or CH$_2$=C(CH$_3$)—CH$_2$—R$_9$
in which R9 has the same meaning as above.

Mention may be made especially of allyl methyl ether, 3-allyloxy-1,2-propanediol (CH$_2$=CHCH$_2$OCH$_2$CH (OH) CH$_2$OH) and 2-allyloxyethanol (CH$_2$=CHCH$_2$OC$_2$H$_4$OH);

(vi) silicone-based (meth)acrylic, (meth)acrylamide or vinyl monomers, such as methacryloxypropyltris(trimethylsiloxy)silane or acryloxypropylpolydimethylsiloxane, or silicone-based (meth)acrylamides.

Among the additional monomers (especially nonionic hydrophilic monomers) that are more particularly preferred, mention may be made, alone or as a mixture, of the following monomers for which the Tg is given in parentheses as a guide:

hydroxyalkyl (meth)acrylates and (meth)acrylamides in which the alkyl group contains 2 to 4 carbon atoms, in particular 2-hydroxyethyl acrylate (Tg=15° C.), 2-hydroxyethyl methacrylate (55° C.), 2-hydroxypropyl methacrylate, 4-hydroxybutyl methacrylate and N-(2-hydroxypropyl)(meth)acrylamide;

(C$_{1-4}$)alkoxy(C$_{1-4}$)alkyl (meth)acrylates and (meth)acrylamides such as methoxyethyl, 2-ethoxyethyl, methoxypropyl and bis(2-ethoxyethyl) (meth)acrylates and (meth)acrylamides; more particularly 2-ethoxyethyl methacrylate;

(meth)acrylamide and N,N-dimethylacrylamide;

(meth)acrylates and (meth)acrylamides containing a group —(OC$_2$H$_4$)$_m$—OR", with m=5 to 300 and R"=H or C$_1$ to C$_4$ alkyl, for example polyethylene glycol (meth)acrylates and (meth)acrylamides (containing a methoxy or hydroxyl end group); and more particularly polyethylene glycol methacrylate containing a hydroxyl end group (n=8, 10, 12, 45, 90 or 200) and polyethylene glycol methacrylate containing a methoxy end group (n=8, 10, 12, 45, 90 or 200)(Tg=−55° C.);

vinyllactams such as vinylpyrrolidone and vinylcaprolactam;

vinyl ethers such as methyl vinyl ether (Tg=−34° C.) and ethyl vinyl ether;

vinylacetamide, N-vinylpyrrolidone and N-vinylcaprolactam;

polysaccharide (meth)acrylates, for instance sucrose acrylate and ethylglucoside (meth)acrylate.

Mention may also be made, among the additional monomers (especially hydrophobic monomers) that are more particularly preferred, alone or as a mixture, of the following monomers for which the Tg is given in parentheses as a guide:

t-butylbenzyl acrylate, t-butylcyclohexyl acrylate, isobornyl acrylate (94° C.), furfuryl acrylate, n-hexyl acrylate (45° C.), t-butyl acrylate (50° C.), cyclohexyl acrylate (19° C.), hydroxyethyl acrylate (15° C.), methyl acrylate (10° C.), ethyl acrylate (−24° C.), isobutyl acrylate (−24° C.), methoxyethyl acrylate (−33° C.), n-butyl acrylate (−54° C.), ethylhexyl acrylate (−50° C.), hexyl acrylate, octyl acrylate, lauryl acrylate, isooctyl acrylate, isodecyl acrylate;

t-butylbenzyl methacrylate, t-butylcyclohexyl methacrylate, isobornyl methacrylate (111° C.), methyl methacrylate (100° C.), cyclohexyl methacrylate (83° C.), ethyl methacrylate (65° C.), benzyl methacrylate (54° C.), isobutyl methacrylate (53° C.), butyl methacrylate (20° C.), n-hexyl methacrylate (−5° C.), ethylhexyl methacrylate, octyl methacrylate, lauryl methacrylate, isooctyl methacrylate, isodecyl methacrylate;

styrene (100° C.), vinylcyclohexane, vinyl acetate (23° C.), methyl vinyl ether (−34° C.), vinyl neononanoate, vinyl neododecanoate;

N-butylacrylamide, N-isopropylacrylamide, N,N-dimethylacrylamide, N,N-dibutylacrylamide, N-t-butylacrylamide, N-octylacrylamide.

Preferably, the copolymers according to the invention may comprise at least one block comprising monomers chosen from isobornyl acrylate, cyclohexyl acrylate (19° C.), ethyl acrylate (10° C.), methyl methacrylate (100° C.), cyclohexyl methacrylate (83° C.), ethyl methacrylate (65° C.), butyl methacrylate (20° C.) and styrene (100° C.).

Preferably, the copolymers according to the invention may comprise at least one block comprising monomers chosen from n-hexyl methacrylate (−5° C.), ethyl acrylate (−24° C.), isobutyl acrylate (−24° C.), n-butyl acrylate (−54° C.), ethylhexyl acrylate (−50° C.); methoxy poly(ethylene glycol) monomethacrylate with a number m of ethyleneglycol units of 8, 12, 90, 180 or 200; methoxy poly(ethylene glycol) monomethacrylamide with m=8, 12, 90, 180 or 200; poly (ethylene glycol)OH (meth)acrylate with m=8, 12, 90, 180 or 200; poly(ethylene glycol)OH (meth)acrylamide with m=8, 12, 90, 180 or 200; vinylpyrrolidone, vinylcaprolactam; methyl vinyl ether and ethyl vinyl ether.

Preferably, the copolymers according to the invention may be copolymers comprising two blocks (diblock), such as:

poly(acrylic acid-co-butyl acrylate)-b-poly-(methyl methacrylate-co-acrylic acid), and poly(methacrylic acid-co-butyl acrylate)-b-poly(methyl methacrylate-co-methacrylic acid).

Preferably, the copolymers according to the invention may be copolymers comprising three blocks (triblock), such as:

poly(methyl methacrylate-co-acrylic acid)-b-poly(acrylic acid-co-butylacrylate)-b-poly(methylmeth-acrylate-co-acrylic acid), poly(methyl methacrylate-co-(meth)acrylic acid)-b-poly (methacrylic acid-co-butyl acrylate)-b-poly(methyl methacrylate-co-methacrylic acid), poly(methyl acrylate-co-acrylic acid)-b-poly-(acrylic acid-co-butyl acrylate)-b-poly(methyl acrylate-co-acrylic acid), poly(acrylic acid-co-butyl acrylate)-b-poly(methyl methacrylate-co-acrylic acid)-b-poly(acrylic acid-co-butyl acrylate);

poly(acrylic acid)-b-poly(acrylic acid-co-butyl acrylate)-b-poly(acrylic acid);

poly(methacrylic acid)-b-poly(methacrylic acid-co-butyl acrylate)-b-poly(methacrylic acid);

poly(acrylic acid-co-cyclohexyl acrylate)-b-poly(acrylic acid-co-butyl acrylate)-b-poly(acrylic acid-co-cyclohexyl acrylate);

poly(acrylic acid-co-butyl acrylate)-b-poly(acrylic acid-co-cyclohexyl acrylate)-b-poly(acrylic acid-co-butyl acrylate);

poly(acrylic acid-co-cyclohexyl methacrylate)-b-poly(acrylic acid-co-butyl acrylate)-b-poly(acrylic acid-co-cyclohexyl methacrylate);

poly(acrylic acid-co-isobornyl acrylate)-b-poly(acrylic acid-co-butyl acrylate)-b-poly(acrylic acid-co-isobornyl acrylate);

poly(methyl methacrylate-co-acrylic acid)-b-poly(acrylic acid-co-methoxypoly(ethylene glycol) monomethacrylate with m=12)-b-poly(methyl methacrylate-co-acrylic acid);

poly(acrylic acid-co-methoxypoly(ethylene glycol) monomethacrylate with m=12)-b-poly(methyl methacrylate-co-acrylic acid)-b-poly(acrylic acid-co-methoxypoly(ethylene glycol) monomethacrylate with m=12).

In general, the monomers constituting each block are preferably chosen so as to promote the separation of the phases between the said blocks, since it is that which will determine the properties of the final polymer.

Preferably, at least one of the blocks of the copolymer according to the invention has a glass transition temperature (Tg) of less than or equal to 20° C.

Preferably also, at least one of the blocks of the copolymer according to the invention has a glass transition temperature (Tg) of greater than or equal to 20° C.

The method for measuring the Tg values is explained before the examples.

In one particular embodiment, the copolymer according to the invention may comprise both a block with a Tg of greater than or equal to 20° C. and a block with a Tg of less than 20° C. The copolymer obtained has an "elastomeric" nature.

It may be a diblock copolymer, comprising only these two blocks, or a triblock copolymer or a copolymer comprising three different blocks, for example a central block with a Tg of less than 20° C. and two blocks at the ends with a Tg of greater than or equal to 20° C.; or alternatively a central block with a Tg of greater than or equal to 20° C. and two blocks at the ends with a Tg of less than or equal to 20° C.

In another embodiment of the invention, the copolymer may comprise at least two different blocks both having a Tg of greater than or equal to 20° C. The said block copolymer then has a "rigid" nature.

The blocks with a Tg of greater than 20° C. may be obtained by homopolymerization of monomers whose homopolymers have a Tg>20° C. or by copolymerization of monomers with a Tg>20° C., but also by copolymerization of monomers with a Tg>20° C. to which may be added monomers with a Tg<20° C.

Similarly, the blocks with a Tg of less than 20° C. may be obtained by homopolymerization of monomers with a Tg<20° C. or copolymerization of monomers with a Tg<20C, but also by copolymerization of monomers with a Tg<20° C. to which may be added monomers with a Tg>20° C.

In another embodiment, the total content in the copolymer of monomers whose homopolymer has a Tg of greater than 20° C. is preferably greater than or equal to 50% by weight, especially from about 70% to 100% by weight, relative to the total weight of the block copolymer. The said block copolymer then also has a "rigid" nature.

In another embodiment of the invention, the copolymer may comprise at least two different blocks both having a Tg of less than or equal to 20° C. The said block copolymer then has an "adhesive" nature.

In another embodiment, the total content in the copolymer of monomers whose homopolymer has a Tg of less than 20° C. is preferably greater than or equal to 60% by weight and especially from about 70% to 100% by weight relative to the total weight of the block copolymer. The said block copolymer then has an "adhesive" nature.

Moreover, in one particular embodiment, the copolymer according to the invention comprises at least one hydrophilic block that has a Tg of greater than or equal to 0° C., for example between 0 and 250° C. and especially between 50° C. and 200° C.

The weight-average molecular mass Mw of the block copolymer according to the invention is preferably between 4000 and 1 000 000, preferably between 10 000 and 800 000, more preferably between 20 000 and 500 000 and especially between 60 000 and 350 000.

Advantageously, the weight-average molecular mass Mw of each block is between 2000 and 500 000, preferably between 5000 and 400 000 and better still between 10 000 and 300 000.

The polymers according to the invention may be diblock polymers of the AB type; or triblock polymers of the ABA, BAB or ABC type with C different from A and B; or alternatively multiblock polymers containing more than three blocks, for example of the type (AB)n, (ABA)n, (BAB)n, (ABC)n or ABCD, with A, B, C and D of different chemical nature.

Preferably, the polymer according to the invention comprises at least 3 successive blocks, two successive blocks being different: for example of ABA or ABC type.

The said polymers may be prepared according to the methods known to those skilled in the art. Among these methods, mention may be made of anionic polymerization, controlled free-radical polymerization, for example with xanthans, dithiocarbamates or dithioesters; polymerization using precursors of nitroxide type; atom-transfer radical polymerization (ATRP); group-transfer polymerization.

For example, the block copolymers according to the invention may be obtained by living or pseudo-living, also known as controlled, free-radical polymerization, described especially in "New Method of Polymer Synthesis", Blackie Academic & Professional, London, 1995, volume 2, page 1.

Controlled free-radical polymerization denotes polymerizations for which the secondary reactions that usually lead to disappearance of the propagating species (termination or transfer reaction) are made very improbable relative to the propagation reaction by means of a free-radical control agent. The imperfection of this mode of polymerization lies in the fact that when the concentrations of free radicals become high relative to the monomer concentration, the secondary reactions become the determining factor and tend to broaden the mass distribution.

As a reminder, it is recalled that living or pseudo-living polymerization is a polymerization for which the growth of the polymer chains ceases only with the disappearance of the monomer. The number-average mass (Mn) grows as the conversion proceeds. Such polymerizations lead to copolymers whose mass dispersity is low, i.e. polymers with a mass polydispersity index (Ip) generally of less than 2.

Anionic polymerization is a typical example of living polymerization.

Pseudo-living polymerization is, itself, combined with controlled free-radical polymerization. Among the main types of controlled free-radical polymerization that may be mentioned are:

free-radical polymerization controlled with nitroxides. Reference may be made especially to patent applications WO 96/24620 and WO 00/71501, which describe the tools for this polymerization and their uses, and also to the articles published by Fischer (Chemical Reviews, 2001, 101, 3581), by Tordo and Gnanou (J. Am. Chem. Soc. 2000, 122, 5929) and by Hawker (J. Am. Chem. Soc. 1999, 121, 3904);

atom-transfer radical polymerization, described especially in patent application WO 96/30421, and which proceeds via reversible insertion onto an organometallic complex in a bond of carbon-halogen type;

free-radical polymerization controlled with sulfur derivatives of xanthate, dithioester, trithiocarbonate or carbamate type, as described in patent applications FR 2821620, WO 98/01478, WO 99/35177, WO 98/58974, WO 99/31144, WO 97/01478 and in the publication from Rizzardo et al. (Macromolecules, 1998, 31, 5559).

By means of these modes of polymerization, the polymer chains of the copolymers grow simultaneously and thus incorporate at each instant the same ratio of comonomers. All the chains thus have the same structures or similar structures, resulting in low composition dispersity. These chains also have a low mass polydispersity index.

Thus, the polymerization may be performed according to the technique of atom transfer (Atom Transfer Radical Polymerization or "ATRP"), or by reaction with a nitroxide, or alternatively according to the technique of "reversible addition-fragmentation chain transfer" ("RAFT"), or finally by the technique of "reverse ATRP".

The technique of atom transfer radical polymerization consists in blocking the growing free-radical species in the form of a bond of C-halide type (in the presence of a metal/ligand complex). This type of polymerization is reflected by control of the mass of the polymers formed and by a low mass dispersity index. In general, atom-transfer radical polymerization is performed by polymerization of one or more monomers that can undergo free-radical polymerization, in the presence of:

an initiator containing at least one transferable halogen atom;

a halogenated compound comprising a transition metal capable of participating in a reduction step with the initiator and a "dormant" polymer chain, which will be known as the "chain-transfer agent"; and a ligand that may be chosen from compounds comprising a nitrogen (N), oxygen (O), phosphorus (P) or sulfur (S) atom, capable of coordinating via a a bond with the said compound comprising a transition metal, the formation of direct bonds between the said compound comprising a transition metal and the polymer in formation being avoided.

The halogen atom is preferably a chlorine or bromine atom.

This process is described in particular in patent application WO 97/18247 and in the article by Matyjasezwski et al. published in JACS, 117, page 5614 (1995).

The technique of free-radical polymerization by reaction with a nitroxide consists in blocking the growing free-radical species in the form of a bond of the type C—O—$NR_aR$ in which $R_a$ and $R_b$ may be, independently of each other, an alkyl radical containing from 2 to 30 carbon atoms or each forming, with the nitrogen atom, a ring containing from 4 to 20 carbon atoms, for instance a 2,2,6,6-tetramethylpiperidyl ring. This polymerization technique is described especially in the articles "Living free radical polymerization: a unique technique for preparation of controlled macromolecular architectures" C J Hawker; Chem. Res. 1997,30,373-82, and "Macromolecular engineering via living free radical polymerizations" published in Macromol. Chem. Phys. 1998, vol. 199, pages 923-935, or alternatively in patent application WO-A-99/03894.

The technique of RAFT polymerization (reversible addition-fragmentation chain transfer) consists in blocking the growing free-radical species in the form of a bond of C—S type. Dithio compounds, for instance dithioesters (–C(S)S—), such as dithiobenzoates, dithiocarbamates (–NC(S)S—) or dithiocarbonates (–OC(S)S—) (xanthates) are used to do this. These compounds allow control of the growth of the chain of a wide range of monomers. However, dithioesters inhibit the polymerization of vinyl esters, while dithiocarbamates are very weakly active with respect to methacrylates, which limits the application of these compounds to a certain extent. This technique is especially described in patent application WO-A-98/58974 from Rhodia and in the article "A more versatile route to block copolymers and other polymers of complex architecture by living radical polymerization: the RAFT process", published in Macromolecules, 1999, volume 32, pages 2071-2074. The already cited patent application WO-A-98/58974 and patent application WO-A-99/31144 from CSIRO relate to the use of dithiocarbamates as "RAFT" reagents.

By varying the ratio of the monomer concentration to the concentration of chain-transfer agent, the molecular mass of the polymer may be modified.

The polymerization generally proceeds in several steps, according to the following general scheme:

a) in a first step, polymerization of the first monomer or monomer mixture is performed to form a macroinitiator or precursor;

b) the polymers may be purified by precipitation and then dried under vacuum, c) in a second step, polymerization of the second block consisting of a monomer or a monomer mixture is performed, at the end of the macroinitiator.

Steps b and c are repeated as many times as necessary according to the number of blocks, which is the case for making diblock polymers of AB type, triblock polymers of ABC type or multiblock polymers $(AB)_n$ or $(ABC)_n$ with A, B and C of different chemical nature.

A difunctional initiator is generally used to make symmetrical triblock polymers of ABA or BAB type.

The chain-transfer agents and solvents may be identical or different in step a) and step b).

The block polymers according to the invention may also be obtained by using the standard free-radical polymerization technique by adding the monomers sequentially. In this case, only control of the nature of the blocks is possible (no mass control).

It is a matter of polymerizing in a first stage a monomer M1 in a polymerization reactor; monitoring, for example kinetically, its consumption over time and then, when M1 has been about 95% consumed, introducing a new monomer M2 into the polymerization reactor. A polymer of block structure of M1-M2 type is thus readily obtained.

The copolymers according to the invention may be present in the compositions according to the invention in an amount of from 0.1% to 60% by weight, preferably 0.5% to 50% by weight, especially 1% to 30% by weight or even 2% to 20% by weight, relative to the total weight of the composition.

They may be present in the composition in dissolved form, for example in water or an organic solvent, or alternatively in the form of an aqueous or organic dispersion. Preferably, they are present in the form of a dispersion of polymer particles in water, the said particles possibly being from 5 to 400 nm and especially 10 to 250 nm in size, measured by light scattering (with a Coulter Counter machine).

One of the characteristics of the copolymers according to the invention is that they do not form a viscoelastic gel in water at 25° C., at a concentration of 5% by weight, especially at a concentration of 10% by weight, or even of 20% by weight.

In particular, the copolymers according to the invention are such that a solution of these copolymers at a concentration of 20% by weight in water has a viscosity at 25° C. of between 1 and 10 000 centipoises (or mPa.s), in particular from 2 to 5000 mPa.s and especially from 5 to 3000 mPa.s.

The viscosity is measured using a Brookfield viscometer, with a module of the needle type (spindle).

A person skilled in the art knows how to select the "speed/time" couple and the spindle of needle type from needles ranging from number 00 to 07, on the basis of his general knowledge, so as to be able to perform the measurement of sparingly viscous liquid compounds. A couple of 35% and a No. 02 needle are preferably used.

The rheological behavior of the copolymers according to the invention may also be illustrated by means of their modulus of elasticity (G') and modulus of viscosity (G") values.

Thus, a solution containing 5% by weight of copolymer in water preferably has a modulus of elasticity less than the modulus of viscosity (G'<G"); in particular, the modulus of elasticity is between 0.1 and 20 Pa, and the modulus of viscosity is between 0.1 and 20 Pa. These modulus values are determined at 25° C., at 1 Hz, with a controlled-stress rheometer (Haake RS 150) equipped with a sand-blasted titanium body fitted with an anti-evaporation device and a cone-plate measuring body 6 cm in diameter and with an angle of 20°. The shear rate or stress frequency is 1 Hz ($s^{-1}$).

The cosmetic or pharmaceutical compositions according to the invention comprise, besides the said polymers, a physiologically acceptable medium, especially a cosmetically or dermatologically acceptable medium, i.e. a medium that is compatible with keratin materials such as facial or bodily skin, the hair, the eyelashes, the eyebrows and the nails.

The composition may thus comprise a hydrophilic medium comprising water or a mixture of water and hydrophilic organic solvent(s), for instance alcohols and especially linear or branched lower monoalcohols containing from 2 to 5 carbon atoms, for instance ethanol, isopropanol or n-propanol, and polyols, for instance glycerol, diglycerol, propylene glycol, sorbitol or pentylene glycol, and polyethylene glycols, or alternatively hydrophilic $C_2$ ethers and $C_2$-$C_4$ aldehydes.

The water or the mixture of water and hydrophilic organic solvents may be present in the composition according to the invention in a content ranging from 0.1% to 99% by weight and preferably from 10% to 80% by weight relative to the total weight of the composition.

The composition may also comprise a fatty phase which especially consists of fatty substances that are liquid at room temperature (in general 25° C.) and/or of fatty substances that are solid at room temperature, such as waxes, pasty fatty substances and gums, and mixtures thereof. These fatty substances may be of animal, plant, mineral or synthetic origin. This fatty phase may also contain lipophilic organic solvents.

As fatty substances that are liquid at room temperature, often referred to as oils, which may be used in the invention, mention may be made of: hydrocarbon-based oils of animal origin such as perhydrosqualene; hydrocarbon-based plant oils such as liquid triglycerides of fatty acids of 4 to 10 carbon atoms, for instance heptanoic or octanoic acid triglycerides, or alternatively sunflower oil, maize oil, soybean oil, grapeseed oil, sesame seed oil, apricot oil, macadamia oil, castor oil, avocado oil, caprylic/capric acid triglycerides, jojoba oil, shea butter oil; linear or branched hydrocarbons of mineral or synthetic origin, such as liquid paraffins and derivatives thereof, petroleum jelly, polydecenes, hydrogenated polyisobutene such as parleam; synthetic esters and ethers, especially of fatty acids, for instance purcellin oil, isopropyl myristate, 2-ethylhexyl palmitate, 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate, triisocetyl citrate, and fatty alcohol heptanoates, octanoates and decanoates; polyol esters, for instance propylene glycol dioctanoate, neopentyl glycol diheptanoate and diethylene glycol diisononanoate; and pentaerythritol esters; fatty alcohols containing from 12 to 26 carbon atoms, for instance octyldodecanol, 2-butyloctanol, 2-hexyldecanol, 2-undecylpentadecanol and oleyl alcohol; partially hydrocarbon-based fluoro oils and/or partially silicone-based fluoro oils; silicone oils, for instance volatile or non-volatile, linear or cyclic polymethylsiloxanes (PDMSs), which are liquid or pasty at room temperature, for instance cyclomethicones, dimethicones, optionally comprising a phenyl group, for instance phenyl trimethicones, phenyltrimethylsiloxydiphenylsiloxanes, diphenylmethyldimethyltrisiloxanes, diphenyl dimethicones, phenyl dimethicones and polymethylphenylsiloxanes; mixtures thereof.

These oils may be present in a content ranging from 0.01% to 90% and better still from 0.1% to 85% by weight relative to the total weight of the composition.

The composition according to the invention may also comprise one or more physiologically acceptable organic solvents.

These solvents may be generally present in a content ranging from 0.1% to 90%, preferably from 0.5% to 85%, more preferably from 10% to 80% and better still from 30% to 50% by weight, relative to the total weight of the composition.

Mention may be made especially, besides the hydrophilic organic solvents mentioned above, of ketones that are liquid at room temperature such as methyl ethyl ketone, methyl isobutyl ketone, diisobutyl ketone, isophorone, cyclohexanone and acetone; propylene glycol ethers that are liquid at room temperature, such as propylene glycol monomethyl ether, propylene glycol monomethyl ether acetate, and dipropylene glycol mono-n-butyl ether; short-chain esters (containing from 3 to 8 carbon atoms in total), such as ethyl acetate, methyl acetate, propyl acetate, n-butyl acetate and isopentyl acetate; ethers that are liquid at 25° C., such as diethyl ether, dimethyl ether or dichlorodiethyl ether; alkanes that are liquid at 25° C., such as decane, heptane, dodecane, isododecane and cyclohexane; aromatic cyclic compounds that are liquid at 25° C., such as toluene and xylene; aldehydes that are liquid at 25° C., such as benzaldehyde and acetaldehyde, and mixtures thereof.

For the purposes of the present invention, the term "wax" means a lipophilic compound that is solid at room temperature (25° C.), which undergoes a reversible solid/liquid change of state, and which has a melting point of greater than or equal to 25° C., which may be up to 120° C. By bringing the wax to the liquid state (melting), it is possible to make it miscible with the oils possibly present and to form a microscopically homogeneous mixture, but, on returning the temperature of the mixture to room temperature, recrystallization of the wax is obtained in the oils of the mixture. The melting point of the wax may be measured using a differential scanning calorimeter (DSC), for example the calorimeter sold under the name DSC 30 by the company Mettler.

The waxes may be hydrocarbon-based waxes, fluoro waxes and/or silicone waxes and may be of plant, mineral, animal and/or synthetic origin. In particular, the waxes have a melting point of greater than 30° C. and better still greater than 45° C. As waxes that may be used in the composition of the invention, mention may be made of beeswax, carnauba wax or candelilla wax, paraffin, microcrystalline waxes, ceresin or ozokerite, synthetic waxes, for instance polyethylene waxes or Fischer-Tropsch waxes, and silicone waxes, for instance alkyl or alkoxy dimethicones containing from 16 to 45 carbon atoms.

The gums are generally polydimethylsiloxanes (PDMSs) of high molecular weight or cellulose gums or polysaccharides, and the pasty substances are generally hydrocarbon-based compounds, for instance lanolins and derivatives thereof, or PDMSs.

The nature and amount of the solid substances depend on the desired mechanical properties and textures. As a guide, the composition may contain from 0.1% to 50% by weight and better still from 1% to 30% by weight of waxes relative to the total weight of the composition.

The composition according to the invention may also comprise, in a particulate phase, pigments and/or nacres and/or fillers usually used in cosmetic compositions.

The composition may also comprise other dyestuffs chosen from water-soluble dyes and/or liposoluble dyes that are well known to those skilled in the art.

The term "pigments" should be understood as meaning white or colored, mineral or organic particles of any shape, which are insoluble in the physiological medium and which are intended to color the composition.

The term "fillers" should be understood as meaning colorless or white, mineral or synthetic, lamellar or non-lamellar particles intended to give body or rigidity to the composition, and/or softness, a matt effect and uniformity to the makeup result.

The term "nacres" should be understood as meaning iridescent particles of any form, produced especially by certain molluscs in their shell, or else synthesized.

The pigments may be present in the composition in a proportion of from 0.01% to 25% by weight and preferably in a proportion of from 3% to 10% by weight of the final composition. They may be white or colored, and mineral or organic. Mention may be made of titanium oxide, zirconium oxide or cerium oxide, and also zinc oxide, iron oxide or chromium oxide, ferric blue, chromium hydrate, carbon black, ultramarines (aluminosilicate polysulfides), manganese pyrophosphate and certain metallic powders such as silver or aluminum powders. Mention may also be made of the D&C pigments and lakes commonly used to give the lips and the skin a makeup effect, which are calcium, barium, aluminum, strontium or zirconium salts.

The nacres may be present in the composition in a proportion of from 0.01% to 20% by weight and preferably in a proportion of from about 3% to 10% by weight. Among the nacres that may be envisaged, mention may be made of natural mother-of-pearl, mica coated with titanium oxide, with iron oxide, with natural pigment or with bismuth oxychloride, and also colored titanium mica.

Among the liposoluble or water-soluble dyes that may be present in the composition, alone or as a mixture, in a proportion of from 0.001% to 15% by weight, preferably 0.01% to 5% by weight and especially from 0.1% to 2% by weight, relative to the total weight of the composition, mention may be made of the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll, methylene blue, cochineal carmine, halo-acid dyes, azo dyes, anthraquinone dyes, copper sulfate, iron sulfate, Sudan brown, Sudan red and annatto, and also beetroot juice and carotene.

The composition according to the invention may also comprise one or more fillers, especially in a content ranging from 0.01% to 50% by weight and preferably ranging from 0.02% to 30% by weight, relative to the total weight of the composition. The fillers may be mineral or organic in any form, platelet-shaped, spherical or oblong. Mention may be made of talc, mica, silica, kaolin, polyamide (Nylon®) powder, poly-p-alanine powder and polyethylene powder, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie) or acrylic acid copolymers (Polytrap® from the company Dow Corning) and silicone resin microbeads (for example Tospearls® from Toshiba), elastomeric polyorganosiloxane particles, precipitated calcium carbonate, magnesium carbonate, magnesium hydrocarbonate, hydroxyapatite, hollow silica microspheres (Silica Beads® from Maprecos), glass or ceramic microcapsules, and metal soaps derived from organic carboxylic acids containing from 8 to 22 carbon atoms and preferably from 12 to 18 carbon atoms, for example zinc, magnesium or lithium stearate, zinc laurate or magnesium myristate.

The composition may also comprise an additional polymer such as a film-forming polymer. According to the present invention, the term "film-forming polymer" means a polymer capable, by itself or in the presence of an auxiliary film-forming agent, of forming a continuous film that adheres to a support and especially to keratin materials. Among the film-forming polymers that may be used in the composition of the present invention, mention may be made of synthetic polymers, of free-radical type or of polycondensate type, polymers of natural origin and mixtures thereof, in particular acrylic polymers, polyurethanes, polyesters, polyamides, polyureas and cellulose-based polymers, for instance nitrocellulose.

The composition according to the invention may also contain ingredients commonly used in cosmetics, such as vitamins, thickeners, gelling agents, trace elements, softeners, sequestering agents, fragrances, acidifying or basifying agents, preserving agents, sunscreens, surfactants, antioxidants, agents for preventing hair loss, antidandruff agents, propellants and ceramides or mixtures thereof. Needless to say, a person skilled in the art will take care to select this or these optional additional compound(s), and/or the amount thereof, such that the advantageous properties of the composition according to the invention are not, or are not substantially, adversely affected by the envisaged addition.

The composition according to the invention may be in the form of a suspension, a dispersion, especially of oil in water by means of vesicles; an optionally thickened or even gelled oily solution; an oil-in-water, water-in-oil or multiple emulsion; a gel or a mousse; an oily or emulsified gel; a dispersion of vesicles, especially of lipid vesicles; a two-phase or multiphase lotion; a spray; a free, compact or cast powder; an anhydrous paste. This composition may have the appearance of a lotion, a cream, a salve, a soft paste, an ointment, a cast or molded solid, especially in stick or dish form, or a compacted solid.

A person skilled in the art will be able to choose the appropriate galenical form, and also the method for preparing it, on the basis of his general knowledge, taking into account firstly the nature of the constituents used, especially their solubility in the support, and secondly the intended application of the composition.

The cosmetic composition according to the invention may be in the form of a care and/or makeup product for bodily or facial skin, the lips and the hair, an antisun product, a self-tanning product or even a haircare product.

It may especially find a particularly advantageous application in the field of making up the skin, semi-mucous membranes, mucous membranes and/or the integuments (nails, eyelashes, eyebrows, bodily hairs and head hairs).

It may also be in the form of a care and/or makeup composition, especially a complexion product such as a foundation, a makeup rouge or an eyeshadow; a lip product such as a lipstick or a lipcare product; a concealer product; a blusher, a mascara or an eyeliner; an eyebrow makeup product, a lip pencil or an eye pencil; a nail product such as a nail varnish or a nailcare product; a body makeup product; a hair makeup product (hair mascara or hair lacquer).

The composition according to the invention may be a protective or care composition for the skin of the face, the neck, the hands or the body, especially an anti-wrinkle composition, an anti-fatigue composition for making the skin radiant, a moisturizing or treating composition; an antisun composition or an artificial tanning composition.

The composition according to the invention may also be a haircare product, especially for holding the hairstyle or for shaping the hair. The haircare compositions are preferably shampoos, hairsetting lotions or gels, blow-drying lotions and fixing and styling compositions such as lacquers or sprays. The lotions may be packaged in various forms, especially in vaporizers, pump-dispenser bottles or in aerosol containers to enable application of the composition in vaporized form or in mousse form.

A subject of the invention is also a cosmetic process for making up or caring for keratin materials, especially bodily or facial skin, the nails, the hair and/or the eyelashes, comprising the application to the said materials of a cosmetic composition as defined above.

The invention also relates to an adhesive composition comprising a copolymer in accordance with the invention. In this case, the copolymer is advantageously present in a content of at least 5% by weight relative to the total weight of the composition.

The adhesive composition may comprise additives such as tackifying resins, plasticizers, such as oils, in which case it will constitute a hot-melt pressure-sensitive adhesive composition (known by the abbreviation HMPSA).

The copolymers of the invention contribute towards improving the mechanical properties of the adhesive compositions, especially when they are exposed to high temperature (for example a strip of the Post-It type placed on a window in full sunlight).

Generally, the oils to be used as plasticizers in HMPSA compositions are oils of trimellitate type, such as trioctyl trimellitate, or alternatively predominantly naphthene-based oils such as Catenex N956 from Shell. It is not recommended to use oils of paraffin type (typically Primol 352 oil from Exxon-Mobil) or of liquid polybutene type (typically Napvis 10) since, under certain conditions, they are incompatible with the copolymer and exude from the mixture.

According to the invention, the tackifying resins are generally colophony-based resins such as Foral AX, colophony ester resins such as Foral F85, resins known by the name pure monomer, such as Krystallex F85,polyterpenes such as Dercolyte A 115 from DRT, hydroxylated polyesters (typically Reagem 5110 from DRT), styrene terpenes (typically Dercolyte TS 105 from DRT), pentaerythritol terpenes (typically Dertoline P2L), and phenol-terpene-based resins (typically Dertophene T105 from DRT).

The composition of the invention may be used as an adhesive to constitute, for example, adhesive tapes, labels and strips, in various fields, such as hygiene, wood, binding and packaging.

The invention also relates to the use of a copolymer as defined above as an ingredient of an adhesive composition.

Finally, the invention relates to thermoplastic compositions. In this case, the copolymer is advantageously present in a content of at least 1% by weight relative to the total weight of the composition.

As additives, such compositions may also comprise one or more thermoplastic polymers, such as polymethyl methacrylate, polystyrene and polyvinyl chloride.

By using the copolymers of the present invention, it will be possible to increase the hardness of the thermoplastic polymers present in the composition.

Finally, the invention relates to the use of a copolymer as defined above as an ingredient in a thermoplastic composition.

The invention is illustrated in greater detail in the examples that follow.

Method for Measuring the Tg

The glass transition temperatures of the blocks may be theoretical Tg values determined from the theoretical Tg values of the constituent monomers of each of the blocks, which may be found in a reference manual such as the Polymer Handbook, 3rd edition, 1989, John Wiley, according to the following relationship, known as Fox's Law:

$$\frac{1}{Tg} = \sum_i \left(\frac{\omega i}{Tgi}\right)$$

wi being the mass fraction of the monomer i in the block under consideration and Tgi being the glass transition temperature of the homopolymer of the monomer i.

Unless otherwise indicated, the Tg values indicated for the blocks are theoretical Tg values.

Molecular Masses

The weight-average molar mass (Mw) and number-average molar mass (Mn) are determined by liquid gel permeation chromatography, or GPC (THF solvent, calibration curve established with linear polystyrene standards, refractometric detector).

The dispersity index is calculated in the following manner: Ip=Mw/Mn.

The GPC is performed with Styragel HR4/7.8×300 mm columns, sold by Waters WAT044225.

The detection is performed with a Waters 410 refractometer.

The eluent is THF, at a flow rate of 1 ml/min.

The injected volume is 50 microliters, at 25° C.

The first block formed is characterized by GPC so as to determine the mass of the first block.

The overall block copolymer is characterized by GPC so as to determine the mass of the total copolymer.

The theoretical weight-average mass of a block is given by the ratio: (weight (g) of monomers constituting the block)/(weight (g) of initiator).

The relative molar proportion of the various monomers in the first block is determined by NMR:

% monomer M1=(% number of moles of M1)/(total number of moles of monomers in the block).

The relative proportion of the various monomers between the first block and the second block is determined by NMR.

General Synthetic Process

The polymers of the examples are synthesized via the ATRP method:
- in the presence of copper (CuI) in the form of a copper halide, for instance CuBr (99% pure) sold by Aldrich, or CuCl (99% pure) sold by Acros,
- with an initiator of the RBr type,
- and a ligand of the amine type. PMDETA or N,N,N',N'',N''-pentamethyldiethylenetriamine from Fluka is used as ligand.

The monomers are passed beforehand through a column of alumina so as to remove any stabilizer.

The synthesis of the diblock takes place using a monofunctional initiator such as ethyl 2-bromoisobutyrate sold by Aldrich, with a degree of purity of 98%.

The synthesis of the triblock proceeds via polymerization starting with the difunctional initiator of the type: 3-[(2-bromo-2-methylpropanoyl)oxy]propyl 2-bromo-2-methylpropanoate: $(CH_3)_2BrC-C(=O)-O-(CH_2)_4-O-C(=O)-C(CH_3)_2Br$.

The polymerization proceeds in several steps:

1st step: formation of the first block by polymerization of the monomer (or monomer mixture) constituting the first block according to the following general scheme:

The appropriate amounts and natures of monomers are introduced into a round-bottomed flask. A flow of argon is bubbled through, with stirring, for 5 minutes, the ligand is then introduced with continued stirring and under a flow of argon, followed by the copper and finally the initiator. Three vacuum/argon degassing cycles are performed.

The mixture is stirred and, when it is homogeneous, it is then placed in an oil bath at a temperature of 90° C. (bath temperature). The polymerization takes place for a given time at 90° C.

The polymer is purified by passing it through a column of alumina so as to separate out the copper-based catalyst.

The polymer is then precipitated in a water/methanol mixture (20/80) under cold conditions (cardice). The first block is thus obtained, which serves as the precursor (or macroinitiator) for the polymerization of the second block: it is a "functional" polymer comprising at its end a function capable of reinitiating the polymerization of a second monomer (or monomer mixture) constituting the second block. This precursor may be represented schematically as: Polymer-Br.

2nd step: formation of the second block by polymerization of the monomer (or monomer mixture) at the end of the macroinitiator (polymer-Br) or (Br-polymer-Br)

The ligand, the solvent and the copper are then added to the macroinitiator, under a flow of argon, followed by addition of the monomer or monomer mixture. The mixture is cooled with liquid nitrogen. Once the mixture has set, three vacuum-argon degassing cycles are performed. The mixture is allowed to return to the liquid state and the reactor is then placed in an oil bath at a temperature of 90° C.

The polymer is purified by passing it through a column of alumina so as to separate out the copper-based catalyst.

The final polymer is then precipitated from a water/methanol mixture (20/80) under cold conditions (cardice).

EXAMPLE 1

Preparation of a poly(butyl acrylate-co-acrylic acid)-b-poly(methyl methacrylate-co-acrylic acid)di-block polymer This polymer is prepared by hydrolysis of a poly-(butylacrylate-co-tert-butyl acrylate)-b-poly(methyl methacrylate-co-tert-butyl acrylate) diblock copolymer.

1/ Synthesis of poly(butyl acrylate-co-tert-butyl acrylate)-b-poly(methyl methacrylate-co-tert-butyl acrylate)

1st step: Synthesis of the poly(butyl acrylate-co-tert-butyl acrylate)-Br macroinitiator According to the general process described above, the mixture of the following monomers is polymerized in the following proportions:

| Reagents | Monomer 1 Butyl acrylate | Monomer 2 tert-Butyl acrylate | Ligand PMDETA: (N,N,N',N'',N''-Pentamethyldiethylenetriamine) | Catalyst CuBr | Initiator Ethyl 2-bromoisobutyrate |
|---|---|---|---|---|---|
| Number of moles | 1.56 | 0.251 | $2.4 \cdot 10^{-3}$ | $2.4 \cdot 10^{-3}$ | $2.4 \cdot 10^{-3}$ |
| Mass (g) | 200 | 32.2 | 0.416 | 0.344 | 0.468 |

Theoretical conversion set in %: 33

Reaction time: 3 hours 35 minutes

Characterization:

Mw theoretical (g/mol): 31 939

Mn measured by GPC (g/mol): 54 900

Mw measured by GPC (g/mol): 59 500

Mp (average mass at the peak measured by GPC) (g/mol): 58 600

Ip=1.1

| Poly (butyl-acrylate-co-tert-butyl-acrylate)-Br | Theoretical acrylate/ total acrylate (by weight) | Mol % measured by NMR | Weight % deduced from the NMR measurement |
|---|---|---|---|
| [Butyl acrylate]/[butyl acrylate + t-butyl acrylate] | 86.1 | 81.0 | 81.0 |
| [tert-Butyl acrylate]/ [butyl acrylate + t-butyl acrylate] | 13.9 | 19.0 | 19.0 |

2nd step: Polymerization of the methyl methacrylate/tert-butyl acrylate mixture at the end of the macroinitiator: poly(butyl acrylate-co-tert-butyl acrylate)-Br The macroinitiator obtained from the first step is placed in a container equipped with an ovoid magnetic bar and is left to evaporate for 12 hours under reduced pressure to remove the maximum amount of possible residual monomers.

GPC is performed just before the synthesis of the second block; the macroinitiator and the final block are measured under the same conditions.

| Reagents | Ligand PMDETA N,N,N',N'',N''-Pentamethyldiethylenetriamine | Macroinitiator Poly(butyl acrylate-co-tert-butyl acrylate)-Br | Catalyst CuBr | Monomer 1 Methyl methacrylate | Monomer 2 tert-Butyl acrylate | Solvent Diphenyl-ether |
|---|---|---|---|---|---|---|
| Number of moles | $2.77\,10^{-4}$ | $2.77\,10^{-4}$ | $2.77\,10^{-4}$ | 0.296 | $2.17\,10^{-2}$ | 0.572 |
| Mass (g) | $4.79\,10^{-2}$ | 16.6 | $2.74\,10^{-2}$ | 30 | 2.78 | 97.4 |

Theoretical degree of conversion: 50%
Reaction time: 10 hours

Characterization of the Diblock Copolymer Formed:
Theoretical MW (g/mol): 118 117
Mn measured by GPC (g/mol): 97 985
Mw measured by GPC (g/mol): 114 579
Mp (average mass at the peak measured by GPC) (g/mol): 115 080
Ip=1.17

| Poly(butyl acrylate-co-tert-butyl acrylate)-b-poly(methyl methacrylate-co-tert-butyl acrylate) | Weight % | Mol % |
|---|---|---|
| Butyl acrylate | 40.0 | 35.2 |
| tert-Butyl acrylate | 11.1 | 9.8 |
| Methyl methacrylate | 48.9 | 55.0 |

% relative to the total amount of monomers

2/ Synthesis of the poly(butyl acrylate-co-acrylic acid)-b-poly(methyl methacrylate-co-acrylic acid) diblock The hydrolysis is performed with trifluoroacetic acid on the tert-butyl acrylate unit. It is used in a six-fold excess of acid relative to the tert-butyl unit.

| Amount of polymer (g) | 16.14 |
|---|---|
| Amount of tert-butyl acrylate (g) | 1.792 |
| Number of moles of tert-butyl acrylate | $1.398\,10^{-2}$ |
| Number of moles of trifluoroacetic acid | $8.389\,10^{-2}$ |
| Amount of trifluoroacetic acid (g) | 9.56 |
| Amount of dichloromethane (g) | 43.3 |

Characterization of the Hydrolyzed Diblock Copolymer:

| Poly(butyl acrylate-co-acrylic acid)-b-poly(methyl methacrylate-co-acrylic acid) | Mol % measured by NMR | Weight % measured by NMR |
|---|---|---|
| Butyl acrylate | 35.2 | 42.0 |
| Acrylic acid | 9.8 | 6.6 |
| Methyl methacrylate | 55.0 | 51.4 |

A diblock copolymer having the distribution below is finally obtained:

in mol %:
poly(methyl methacrylate 97.1%-co-acrylic acid 2.9%)-b-poly(butyl acrylate 81.0%-co-acrylic acid 19.0%)
in weight %:
poly(methyl methacrylate 97.9%-co-acrylic acid 2.1%)-b-poly(butyl acrylate 88.4%-co-acrylic acid 11.6%)

3/ Aqueous Dissolution/dispersion of the Polymer

The neutralization of the acid units is performed by adding 2-amino-2-methylpropanol (AMP).

The polymer is dissolved in THF, and the AMP and water are then added with vigorous stirring using an Ultra-Turrax blender.

A sparingly viscous white milk with bluish glints is obtained.

Particle size on a Coulter machine: 390 nm
Dry extract of the solution: 18.1% by weight

EXAMPLE 2

Preparation of a poly(methyl methacrylate-co-methacrylic acid)-b-poly(butyl acrylate-co-methacrylic acid)-b-poly(methyl methacrylate-co-methacrylic acid) triblock.

This polymer is prepared by hydrolysis of a poly(methyl methacrylate-co-tert-butyl methacrylate)-b-poly(butyl acrylate-co-tert-butyl methacrylate)-b-poly(methyl methacrylate-co-tert-butyl methacrylate) triblock copolymer.

1/ Synthesis of poly(methyl methacrylate-co-tert-butyl methacrylate)-b-poly(butyl acrylate-co-tert-butyl methacrylate)-b-poly(methyl methacrylate-co-tert-butyl methacrylate)

1st step: Synthesis of the difunctional macroinitiator Br-poly(tert-butyl acrylate-co-tert-butyl methacrylate)-Br This macroinitiator is synthesized by polymerization of the monomer mixture using a difunctional initiator: $(CH_3)_2BrC$—$C(=O)$—$O$—$(CH_2)_4$—$O$—$C(=O)$—$C(CH_3)_2Br$ Preparation of the Difunctional Polymerization Initiator A difunctional initiator is prepared according to the following reaction scheme:

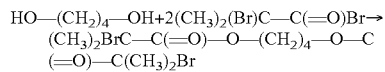

HO—(CH$_2$)$_4$—OH+2(CH$_3$)$_2$(Br)C—C(=O)Br→
(CH$_3$)$_2$BrC—C(=O)—O—(CH$_2$)$_4$—O—C(=O)—C(CH$_3$)$_2$Br 18 g (0.2 mol) of 1,4-butanediol are mixed with 100 g of tetrahydrofuran and the mixture is allowed to equilibrate for 10 minutes at room temperature. 40.4 g (0.4 mol) of triethylamine are then added slowly, over a period of 30 minutes, so that the temperature of the solution does not increase suddenly. 92 g (0.4 mol) of 2-bromoisobutyryl bromide are then added very slowly, over a period of 3 hours and with cooling to 5° C. During this addition, gradual yellowing of the reaction solution is observed. Stirring is continued overnight at 25° C. and the temperature is then allowed to rise gradually to room temperature.

The reaction solution is concentrated by evaporating off the THF and the residue is precipitated from water. The aqueous phase is then extracted 3 times with ethyl ether, and the ether phase is then dried over magnesium sulfate.

After evaporating off the ether, 63 g of bis(n-butyl 1,4-bromoisobutyrate) are thus obtained, which corresponds to a yield of 80%.

According to the general procedure described above, the mixture of monomers below is polymerized in the following proportions:

Polymerization conversion: 40% by weight

Reaction time: 9 hours 15 minutes

Characterization:

Theoretical MW (g/mol): 73 259

Mn measured by GPC (g/mol): 68 400

Mw measured by GPC (g/mol): 77 294

Mp (average mass at the peak measured by GPC) (g/mol): 75 292

Ip=1.13

| Br-Poly(butyl acrylate-co-tert-butyl methacrylate)-Br | % Acrylate/ total theoretical % acrylate by weight | Mol % measured by NMR | Weight % deduced from the NMR measurement |
|---|---|---|---|
| Butyl acrylate | 88.7 | 80.2 | 78.5 |
| tert-butyl methacrylate | 11.3 | 19.8 | 21.5 |

| Reagents | Monomer 1 Butyl acrylate | Monomer 2 tert-Butyl methacrylate | Ligand PMDETA: (N,N,N',N'',N''-Pentamethyldiethylenetriamine) | Catalyst CuBr | Initiator Above difunctional polymerization initiator |
|---|---|---|---|---|---|
| Number of moles | 2.34 | 0.268 | 3.69 10$^{-3}$ | 3.69 10$^{-3}$ | 1.85 10$^{-3}$ |
| Mass in g | 300 | 38.1 | 0.64 | 0.53 | 0.716 |

2nd step: Polymerization of the methyl methacrylate-tert-butyl methacrylate mixture at the end of the difunctional precursor Br-poly(butyl acrylate-co-tert-butyl methacrylate)-Br The precursor is introduced into a container equipped with an ovoid magnetic bar and is left to evaporate for 12 hours under reduced pressure to remove the maximum amount of possible residual monomers.

| Reagents | Ligand PMDETA | Precursor Br-poly(butyl acrylate-co-tert-butyl methacrylate)-Br | Catalyst CuCl | Monomer 1 Methyl methacrylate | Monomer 2 tert-Butyl methacrylate | Solvent Diphenyl ether |
|---|---|---|---|---|---|---|
| Number of moles | 2.23 10$^{-4}$ | 1.11 10$^{-4}$ | 2.23 10$^{-4}$ | 8.25 10$^{-2}$ | 3.87 10$^{-2}$ | 0.191 |
| Mass in g | 2.23 10$^{-4}$ | 8.60 | 2.23 10$^{-4}$ | 8.26 | 5.51 | 32.5 |

Polymerization conversion: 30% by weight

Reaction time: 70 min

Characterization of the Triblock Copolymer:

Theoretical Mw (g/mol): 114 222

Mn measured by GPC (g/mol): 103 727

Mw measured by GPC (g/mol): 133 295

Mp (average mass at the peak measured by GPC) (g/mol): 114 983

Ip=1.29

| Poly(methyl methacrylate-co-tert-butyl methacrylate)-b-poly(butyl acrylate-co-tert-butyl methacrylate)-b-poly(methyl methacrylate-co-tert-butyl methacrylate) | Mol % measured by NMR | Weight % deduced from the NMR measurement |
|---|---|---|
| Butyl acrylate | 47.3 | 48.7 |
| tert-Butyl methacrylate | 25.5 | 21.9 |
| Methyl methacrylate | 27.2 | 29.2 |

2/ Production of poly(methyl methacrylate-co-methacrylic acid)-b-poly(butyl acrylate-co-methacrylic acid)-b-poly(methyl methacrylate-co-methacrylic acid)

To do this, the poly(methyl methacrylate-co-tert-butyl methacrylate)-b-poly(butyl acrylate-co-tert-butyl methacrylate)-b-poly(methyl methacrylate-co-tert-butyl methacrylate) prepared above is hydrolyzed.

The hydrolysis is performed with trifluoroacetic acid on the tert-butyl acrylate unit. A five-fold excess of acid relative to the tert-butyl unit is used. The polymer is dissolved at 30% in dichloromethane. The reaction takes place at room temperature for 16 hours.

| | |
|---|---|
| Amount of polymer in g | 14 |
| Amount of tert-butyl methacrylate in g in the polymer | 4.09 |
| Number of moles of tert-butyl methacrylate | $2.87 \cdot 10^{-2}$ |
| Number of moles of trifluoroacetic acid | 0.144 |
| Trifluoroacetic acid in g | 16.4 |
| Solvent: dichloromethane in g | 32.7 |

Characterization of the Hydrolyzed Triblock Copolymer:

| Poly(methyl methacrylate-co-methacrylic acid)-b-poly(butyl acrylate-co-methacrylic acid)-b-poly(methyl methacrylate-co-methacrylic acid) | Mol % measured by NMR | Weight % deduced from the NMR measurement |
|---|---|---|
| Butyl acrylate | 47.3 | 55.2 |
| Methacrylic acid | 25.5 | 20 |
| Methyl methacrylate | 27.2 | 24.8 |

A triblock polymer having the following distribution (weight % in the triblock) is finally obtained:

poly(methyl methacrylate 34.9-co-methacrylic acid 15.1) 15%-b-poly(butyl acrylate 86-co-methacrylic acid 14) 70%-b-poly(methyl methacrylate 34.9-co-methacrylic acid 15.1)15%

3/ Aqueous Dissolution/dispersion of the Polymer

The neutralization of the acid units is performed by adding AMP to the water. The polymer thus obtained is water-soluble.

Dry extract of the solution: 5.1% by weight pH=8.5

Viscosity in water: 47.6 mPa.s (measured with a No. 02 needle with a 38.1% couple), at 25° C. and at a concentration of 20% by weight.

EXAMPLE 3

The polymer of Example 1 is dissolved in water, in a proportion of 15 g of polymer in 100 ml of water (15% by weight solution).

A haircare composition that may be packaged in a pump-dispenser bottle to be applied to the hair is obtained; this composition gives styling to the head of hair.

EXAMPLE 4

The polymer of Example 2 is dissolved in water, in a proportion of 15 g of polymer in 100 ml of water (15% by weight solution).

A haircare composition that may be packaged in a pump-dispenser bottle to be applied to the hair is obtained; this composition gives styling to the head of hair.

EXAMPLE 5

The polymer of Example 1 is dissolved in ethyl acetate, in a proportion of 25 g of polymer in 100 ml of ethyl acetate (25% by weight solution).

After addition of the appropriate dyestuffs, a nail varnish that may be applied to the nails is obtained.

The invention claimed is:

1. A linear ethylenic block copolymer comprising at least one first block, and at least one second block, each block of the copolymer formed from at least one ionic hydrophilic monomer and at least one additional monomer, the ionic hydrophilic monomer being the same or different from one block to another, the ionic hydrophilic monomer being present in each block in an amount ranging from 2% to 100% by weight relative to the weight of the block copolymer;

wherein the additional monomer is nonionic hydrophilic monomers, hydrophobic monomers, or mixtures thereof, and is selected from the group consisting of:

(i) ethylenic hydrocarbons containing 2 to 10 carbons;

(ii) (meth)acrylates of formula:

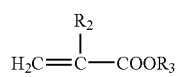

wherein $R_2$ is chosen from hydrogen and methyl, and $R_3$ is chosen from:

linear and branched alkyl groups of 1 to 30 carbon atoms, optionally intercalated with at least one hetero atom chosen from O, N, S and P; the alkyl groups optionally substituted with at least one substituent chosen from OH, halogen atoms chosen from Cl, Br, I and F, and groups chosen from:

—Si(R₄R₅R₆) and —Si(R₄R₅)O, wherein R₄, R₅ and R₆, which may be identical or different, are chosen from hydrogen atoms, C1-C6 alkyl groups, and phenyl groups;

C3-C12 cycloalkyl groups,

C3-C20 aryl groups,

C4-C30 aralkyl groups having a C1-C8 alkyl group, 4- to 12-membered aromatic and non-aromatic heterocyclic groups containing at least one hetero atom chosen from O, N and S, heterocycloalkyl group having a C1-C4 alkyl group, wherein the cycloalkyl, aryl, aralkyl, heterocyclic and heterocycloalkyl groups are optionally substituted with at least one substituent chosen from hydroxyl groups, halogen atoms, and linear and branched C1-C4 alkyl groups optionally intercalated with at least one hetero atom chosen from O, N, S and P, the C1-C4 alkyl groups also optionally substituted with at least one substituent chosen from —OH, halogen atoms chosen from Cl, Br, I and F, and groups —Si(R₄R₅R₆) and —Si(R₄R₅)O, wherein R₄R₅ and R₆, which may be identical or different, are chosen from hydrogen atoms, C1-C6 alkyl groups, and phenyl groups, —(OC₂H₄)ₘ—OR" groups, wherein m ranges from 5 to 300 and R" is chosen from hydrogen atoms and C1-C30 alkyl groups; (OC₃H₆)ₘ—OR" groups, wherein m ranges from 5 to 300 and R" is chosen from hydrogen and C1-C30 alkyl groups; and random or block mixtures of groups (OC₂H₄)ₘ and (OC₃H₆)ₘ, wherein m ranges from 5 to 300;

(iii) (meth)acrylamides of formula:

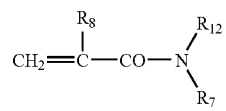

wherein R₈ is chosen from hydrogen atoms and methyl groups;

and R₇ and R₁₂, which may be identical or different, are chosen from;

hydrogen atoms; and linear and branched alkyl groups of 1 to 30 carbon atoms optionally intercalated with at least one hetero atom chosen from O, N, S and P; the alkyl groups optionally substituted with at least one substituent chosen from —OH, halogen atoms chosen from Cl, Br, I and F, and —Si(R₄R₅R₆) and —Si(R₄R₅)O groups, wherein R₄, R₅ and R₆ are chosen from hydrogen atoms, C1-C6 alkyl groups, and phenyl groups;

C3-C12 cycloalkyl groups,

C3-C20 aryl groups,

C4-C30 aralkyl groups having a C1-C8 alkyl group,

C4- to 12-membered aromatic and non-aromatic heterocyclic groups containing at least one hetero atom chosen from O, N and S, heterocycloalkyl group having a C1-C4 alkyl group, wherein the cycloalkyl, aryl, aralkyl, heterocyclic and heterocycloalkyl groups are optionally substituted with at least one substituent chosen from hydroxyl groups, halogen atoms, and linear and branched C1-C4 alkyl groups optionally intercalated with at least one hetero atom chosen from O, N, S and P, the alkyl groups optionally substituted with at least one substituent chosen from —OH, halogen atoms chosen from Cl, Br, I and F, and —Si(R₄R₅R₆) and —Si(R₄R₅)O groups, wherein R₄, R₅ and R₆, which may be identical or different, are chosen from hydrogen atoms, C1-C6 alkyl groups, and phenyl groups;

—(OC₂H₄)ₘ—OR" groups, wherein m ranges from 5 to 300 and R" is chosen from hydrogen atoms and C1-C30 alkyl groups; —(OC₃H₆)ₘ—OR" groups, wherein m ranges from 5 to 300 and R" is chosen from hydrogen atoms and C1-C30 alkyl groups; and random or block mixtures of (OC₂H₄)ₘ and (OC₃H₆)ₘ groups, wherein m ranges from 5 to 300;

(iv) vinyl compounds of formula:

CH₂=CH—R₉, wherein R₉ is chosen from hydroxyl groups; a halogen chosen from Cl and F; NH₂ groups; OR₁₁ groups in which R₁₁ is chosen from phenyl groups and C1-C12 alkyl groups such that the at least one additional monomer is chosen from vinyl and allylic ethers; acetamide groups (NHCOCH₃); OCOR₁₂ groups wherein R₁₂ is chosen from linear and branched alkyl groups of 2 to 12 carbons such that the at least one additional monomer is chosen from vinyl and allylic esters, C3-C12 cycloalkyls, C3-C20 aryls and C4-C30 arallyls; or R₉ is chosen from:

linear and branched alkyl groups containing 1 to 30 carbon atoms optionally intercalated with at least one hetero atom chosen from O, N, S and P; the alkyl group optionally substituted with at least one substituent chosen from —OH, halogen atoms chosen from Cl, Br, I and F, and —Si(R₄R₅R₆) and —Si(R₄R₅)O groups, wherein R₄, R₅ and R₆, which may be identical or different, are chosen from hydrogen atoms, C1-C6 alkyl groups, and phenyl groups;

C3-C12 cycloalkyl groups,

C3-C20 aryl groups,

C4-C30 arylalkyl or alkylaryl groups having a C1-C8 alkyl group, 4- to 12-membered aromatic and non-aromatic heterocyclic groups containing at least one hetero atom chosen from O, N and S;

heterocycloalkyl groups having a C1-C4 alkyl group, wherein the cycloalkyl, aryl, aralkyl, heterocyclic and heterocycloalkyl groups are optionally substituted with at least one substituent chosen from hydroxyl groups, halogen atoms, and linear and branched C1-C4 alkyl groups optionally intercalated with at least one hetero atom chosen from O, N, S and P, the alkyl groups optionally substituted with at least one substituent chosen from —OH, halogen atoms chosen from Cl, Br, I and F, and —Si(R₄R₅R₆) and —Si(R₄R₅)O groups, wherein R₄, R₅ and R₆, which may be identical or different, are chosen from hydrogen atoms, C1-C6 alkyl groups, and phenyl groups;

(v) allylic compounds of formula:

CH₂=CH—CH₂—R₉ and CH₂=C(CH₃)—CH₂—R₉, wherein R₉ has the same meaning as above; and (vi) silicone-based (meth)acrylic, (meth)acrylamide and vinyl monomers.

2. The linear ethylenic block copolymer according to claim 1, wherein the at least one ionic hydrophilic monomer is present in each block in an amount ranging from 3% to 25% by weight relative to the weight of the block.

3. The linear ethylenic block copolymer according to claim 2, wherein the at least one hydrophilic monomer is present in each block in an amount ranging from 8% to 30% by weight relative to the weight of the block.

4. The linear ethylenic block copolymer according to claim 1, wherein the copolymer comprises two blocks (diblock) or three blocks (triblock), each of the blocks comprising at least one ionic hydrophilic monomer, present in an amount ranging from 2% to 100% by weight relative to the weight of the block.

5. The linear ethylenic block copolymer according to claim 1, wherein the at least one ionic hydrophilic monomer is chosen from anionic, cationic and amphoteric hydrophilic monomers, and mixtures thereof.

6. The linear ethylenic block copolymer according to claim 1, wherein each of the blocks comprises at least one anionic hydrophilic monomer and/or at least one cationic hydrophilic monomer.

7. The linear ethylenic block copolymer according to claim 1, wherein at least one block comprises both at least one cationic hydrophilic monomer and at least one anionic hydrophilic monomer.

8. The linear ethylenic block copolymer according to claim 1, wherein at least one of the blocks comprises at least one anionic hydrophilic monomer of formula (I):

(I)

wherein:
R$_1$ is chosen from a hydrogen atom and linear and branched hydrocarbon-based radicals of C$_p$H$_{2p+1}$ type, wherein p is an integer from 1 to 12;
Z is a divalent group chosen from —COO—, —CONH—, —CONCH$_3$—, —OCO— and —O—;
x is 0 or 1;
R$_2$ is chosen from linear, branched and cyclic, optionally aromatic, saturated and unsaturated divalent carbon-based radicals of 1 to 30 carbon atoms, which may comprise 1 to 30 hetero atoms chosen from O, N, S and P;
Y is a group chosen from —COOH, —SO$_3$H, —OSO$_3$H, —PO(OH)$_2$ and —OPO(OH)$_2$;
m is equal to 0 or 1.

9. The linear ethylenic block copolymer according to claim 8, wherein R$_1$ is chosen from methyl, ethyl, propyl and butyl.

10. The linear ethylenic block copolymer according to claim 8, wherein Z is chosen from —COO— and —CONH—.

11. The linear ethylenic block copolymer according to claim 8, wherein x is 1.

12. The linear ethylenic block copolymer according to claim 8, wherein R$_2$ is chosen from:
alkylene radicals;
phenylene radicals —C$_6$H$_4$—, which may be ortho, meta or para, optionally substituted with a C1-C12 alkyl radical optionally comprising 1 to 8 hetero atoms chosen from O, N, S, and P;
benzylene radicals —C$_6$H$_4$-CH$_2$—, optionally substituted with a C1-C12 alkyl radical optionally comprising 1 to 8 hetero atoms chosen from O, N, S and P;
radicals chosen from —CH$_2$—CHOH—, —CH$_2$—CH$_2$—CHOH—, —CH$_2$—CH$_2$—CH(NH$_2$)—, —CH$_2$—CH(NH$_2$)—, —CH$_2$—CH$_2$—CH(NHR')—, —CH$_2$—CH(NHR')—, —CH$_2$—CH$_2$—CH(NR'R")—, —CH$_2$-CH(NR'R")—, and —CH$_2$—CH═CH—, wherein R' and R" are chosen from linear and branched C1-C18 alkyl radicals.

13. The linear ethylenic block copolymer according to claim 12, wherein the alkylene radicals are chosen from methylene, ethylene, propylene, n-butylene, isobutylene, tert-butylene, n-hexylene, n-octylene, n-dodecylene, n-octadecylene, n-tetradecylene and n-docosanylene.

14. The linear ethylenic block copolymer according to claim 12, wherein R$_2$ is chosen from radicals chosen from —CH$_2$—CHOH—, —CH$_2$—CH$_2$—CHOH—, —CH$_2$—CH$_2$—CH(NH$_2$)—, —CH$_2$—CH(NH$_2$)—, —CH$_2$—CH$_2$—CH(NHR')—, —CH$_2$—CH(NHR')—, —CH$_2$—CH$_2$—CH(NR'R")—, —CH$_2$—CH(NR'R")—, and —CH$_2$—CH═CH—, wherein R' and R" are chosen from methyl and ethyl radicals.

15. The linear ethylenic block copolymer according to claim 6, wherein the at least one anionic hydrophilic monomer is chosen from acrylic acid, methacrylic acid, crotonic acid, itaconic acid, fumaric acid, maleic acid, diacrylic acid, dimethylfumaric acid, citraconic acid, acrylamido-propane-sulfonic acid, 2-acrylamido-2-methylpropane-sulfonic acid, styrenesulfonic acid, vinylbenzoic acid, vinylphosphoric acid, vinylsulfonic acid, vinylbenzene-sulfonic acid, acrylamidoglycolic acid of formula CH$_2$═CH—CONHCH(OH)COOH, vinylphosphonic acid, 2-carboxy-ethyl (meth)acrylate, sulfopropyl methacrylate or acrylate (CH$_2$═C(CH$_3$)CO$_2$(CH$_2$)$_3$SO$_3$H), sulfoethyl methacrylate or acrylate and vinyl methyl sulfone, 2-(methacryloyloxy) ethyl phosphate of formula CH$_2$═C(CH$_3$)COOC$_2$H$_4$OP(O)(OH)$_2$; diallyl maleate of formula C$_3$H$_5$—CO$_2$—CH═CH—CO$_2$—C$_3$H$_5$, carboxylic anhydrides bearing a vinyl bond, salts thereof; and mixtures thereof.

16. The linear ethylenic block copolymer according to claim 15, wherein the at least one anionic hydrophilic monomer is maleic anhydride.

17. The linear ethylenic block copolymer according to claim 1, wherein at least one of the blocks comprises at least one cationic hydrophilic monomer of formula (II):

(II)

wherein:
R$_1$ is chosen from a hydrogen atom and linear and branched hydrocarbon-based radicals of C$_p$H$_{2p+1}$ type, wherein p is an integer from 1 to 12;
Z is a divalent group chosen from —COO—, —CONH—, —CONCH$_3$—, —OCO— and —O—;
x is 0 or 1;
R$_2$ is chosen from linear, branched and cyclic, optionally aromatic, saturated and unsaturated divalent carbon-based radicals of 1 to 30 carbon atoms, which may comprise 1 to 30 hetero atoms chosen from O, N, S and P;
m is equal to 0 or 1;
X is chosen from:
(a) groups of formula —N—R$_6$R$_7$, wherein R$_6$ and R$_7$, independently of each other, are chosen from:
(i) hydrogen atoms;
(ii) linear, branched and cyclic, saturated and unsaturated, optionally aromatic alkyl groups containing from 1 to 30 carbon atoms, which may comprise 1 to 10 hetero atoms chosen from O, N, S and P;

(iii) alkylene oxide groups of formula —$(R_8O)_yR_9$, wherein $R_8$ is chosen from linear and branched C2-C4 alkyl radicals, $R_9$ is chosen from hydrogen and linear and branched C1-C30 alkyl radicals, and y ranges from 1 to 250;

(iv) $R_6$ and $R_7$ may form with the nitrogen atom a saturated or unsaturated optionally aromatic ring containing in total 5, 6, 7 or 8 atoms; the ring optionally being fused with at least one other saturated or unsaturated, optionally aromatic ring comprising 5, 6 or 7 atoms; and (b) groups of formula —$R'_6$—N—$R'_7$—, wherein $R'_6$ and $R'_7$ form with the nitrogen atom a saturated or unsaturated, optionally aromatic ring, comprising in total 5, 6, 7 or 8 atoms; the ring optionally being fused with at least one other saturated or unsaturated, optionally aromatic ring comprising 5, 6 or 7 atoms.

18. The linear ethylenic block copolymer according to claim 17, wherein the saturated or unsaturated, optionally aromatic ring formed by $R_6$ and $R_7$ with the nitrogen atom to which they are attached comprises 4, 5, or 6 carbon atoms and/or 2 to 4 hetero atoms chosen from O, S, and N; and the at least one other saturated or unsaturated, optionally aromatic ring optionally fused with said ring formed by $R_6$ and $R_7$ with the nitrogen atom to which they are attached comprises 4, 5, 6, or 7 carbon atoms and/or 2 to 4 hetero atoms chosen from O, S, and N; and the saturated or unsaturated, optionally aromatic ring formed by $R'_6$ and $R'_7$ with the nitrogen atom to which they are attached comprises 4, 5, or 6 carbon atoms and/or 2 to 4 hetero atoms chosen from O, S, and N; and the at least one other saturated or unsaturated, optionally aromatic ring optionally fused with said ring formed by $R'_6$ and $R'_7$ with the nitrogen atom to which they are attached comprises 4, 5, 6, or 7 carbon atoms and/or 2 to 4 hetero atoms chosen from O, S, and N.

19. The linear ethylenic block copolymer according to claim 17, wherein at least one of $R_6$ and $R_7$ is chosen from methyl, ethyl, propyl, isopropyl, n-butyl, t-butyl, isobutyl, lauryl and stearyl groups.

20. The linear ethylenic block copolymer according to claim 6, wherein the at least one cationic hydrophilic monomer is chosen from:

2-vinylpyridne, 4-vinylpyridine, allylamine and allylpyridine;
aminoalkyl (meth)acrylates;
aminoalkyl(meth)acrylamides;
vinylamine, vinylimidazole and 2-(diethylamino)-ethylstyrene;
N-vinylimidazole, N-vinyl-2-methylimidazole, N-vinylcarbazole;

and salts thereof and/or the quaternized forms thereof, and mixtures thereof.

21. The linear ethylenic block copolymer according to claim 20, wherein the at least one cationic hydrophilic monomer is chosen from [N,N-di-(C1-C4)alkylamino] (C1-C6) alkyl (meth)acrylates and [N—(C1-C4)alkylamino] (C1-C6) alkyl (meth)acrylates.

22. The linear ethylenic block copolymer according to claim 21, wherein the at least one cationic hydrophilic monomer is chosen from N,N-dimethylaminoethyl (meth)acrylate, N,N-diethylaminoethyl (meth)acrylate, 2-aminoethyl (meth) acrylate and 2-(N-tert-butylamino) ethyl (meth)acrylate.

23. The linear ethylenic block copolymer according to claim 20, wherein the at least one cationic hydrophilic monomer is chosen from [N,N-di-(C1-C4)alkylamino] (C1-C6) alkyl(meth)acrylamides and [N—(C1-C4)alkylamino] (C1-C6)alkyl(meth)acrylamides.

24. The linear ethylenic block copolymer according to claim 22, wherein the at least one cationic hydrophilic monomer is chosen from N,N-dimethylaminopropyl (meth)acrylamide, N,N-dimethylaminoethyl (meth) acrylamide, and 3-aminopropyl (meth) acrylamide.

25. The linear ethylenic block copolymer according to claim 1, wherein at least one of the blocks comprises at least one amphoteric monomer of formula (III):

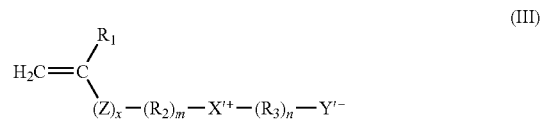

(III)

wherein:
$R_1$ is chosen from a hydrogen atom and linear and branched hydrocarbon-based radicals of $C_pH_{2p+1}$ type, wherein p is an integer from 1 to 12;

Z is a divalent group chosen from —COO—, —CONH—, —CONCH$_3$—, —OCO— and —O—;

x is 0 or 1;

$R_2$ is chosen from linear, branched and cyclic, optionally aromatic, saturated and unsaturated divalent carbon-based radicals of 1 to 30 carbon atoms, which may comprise 1 to 30 hetero atoms chosen from O, N, S and P;

m is equal to 0 or 1;

$X'^+$ is chosen from divalent groups of formula —$N^+R'_6R'_7$—, wherein $R'_6$ and $R'_7$, independently of each other, are chosen from:

(i) hydrogen atoms;
(ii) linear, branched and cyclic, optionally aromatic alkyl groups, containing from 1 to 30 carbon atoms, which may comprise 1 to 8 hetero atoms chosen from O, N, S and P;
(iii) alkylene oxide groups of formula —$(R_8O)_yR_9$, wherein $R_8$ is chosen from linear and branched C2-C4 alkyl radicals, $R_9$ is chosen from hydrogen and linear and branched C1-C30 alkyl radicals and y ranges from 1 to 250;
(iv) $R'_6$ and $R'_7$ may form with the nitrogen atom a saturated or unsaturated, optionally aromatic ring comprising in total 5, 6, 7 or 8 atoms; the ring optionally being fused with at least one other saturated or unsaturated, optionally aromatic ring comprising 5, 6, 7 or 8 atoms;

$Y'^-$ is a group chosen from —COO$^-$, —SO$_3^-$, —OSO$_3^-$, —PO$_3^{2-}$ and —PO$_4^{2-}$;

$R_3$ is chosen from saturated and unsaturated, optionally aromatic, linear, branched and cyclic divalent carbon-based radicals of 1 to 30 carbon atoms, which may comprise 1 to 18 hetero atoms chosen from O, N, S and P;

n is 0 or 1.

26. The linear ethylenic block copolymer according to claim 25, wherein X is chosen from divalent groups of formula —$N^+R'_6R'_7$—, wherein $R'_6$ and $R'_7$ form with the nitrogen atom a saturated or unsaturated, optionally aromatic ring containing in total 5, 6, 7 or 8 atoms, wherein the total of 5, 6, 7, or 8 atoms comprise 4, 5, 6, or 7 carbon atoms and/or 2 to 4 hetero atoms chosen from O, S, and N; the ring optionally being fused with at least one other saturated or unsaturated, optionally aromatic ring comprising 5, 6, 7, or 8 atoms, wherein the 5, 6, 7, or 8 atoms comprise 4, 5, 6, or 7 carbon atoms and/or 2 to 4 hetero atoms chosen from O, S, and N.

27. The linear ethylenic block copolymer according to claim 25, wherein at least one of $R'_6$ and $R'_7$ is chosen from methyl, ethyl, propyl, isopropyl, n-butyl, t-butyl or isobutyl groups.

28. The linear ethylenic block copolymer according to claim 25, wherein $R_3$ is chosen from:
alkylene radicals;
phenylene radicals —$C_6H_4$—, which may be ortho, meta or para, optionally substituted with a C1-C12 alkyl radical optionally comprising 1 to 5 hetero atoms chosen from O, N, S, F, Si and P;
benzylene radicals —$C_6H_4$—$CH_2$—, which are optionally substituted with a C1-C12 alkyl radical optionally comprising 1 to 5 hetero atoms chosen from O, N, S and P.

29. The linear ethylenic block copolymer according to claim 28, wherein $R_3$ is chosen from methylene, ethylene, propylene, n-butylene, isobutylene, tert-butylene, n-hexylene, n-octylene, n-dodecylene, n-octadecylene, n-tetradecylene, n-docosanylene.

30. The linear ethylenic block copolymer according to claim 25, wherein the at least one amphoteric hydrophilic monomer is chosen from N,N-dimethyl-N-(2-meth-acryloyloxyethyl)-N-(3-sulfopropyl) ammonium betaine, N,N-dimethyl-N-(3-methacrylamidopropyl)-N-(3-sulfo-propyl)ammonium betaine and 1-(3-sulfopropyl)-2-vinyl-pyridinium betaine, and mixtures thereof.

31. The linear ethylenic block copolymer according to claim 1, wherein the copolymer comprises the at least one ionic hydrophilic monomer in an amount ranging from 4% to 100% by weight relative to the total weight of the copolymer.

32. The linear ethylenic block copolymer according to claim 30, wherein the copolymer comprises the at least one ionic hydrophilic monomer in an amount ranging from 10% to 30% by weight relative to the total weight of the copolymer.

33. The linear ethylenic block copolymer according to claim 1, wherein the at least one additional monomer is chosen from nonionic hydrophilic monomers present in an amount ranging from 0 to 98% by weight relative to the total weight of the at least one block.

34. The linear ethylenic block copolymer according to claim 33, wherein the at least one additional monomer is chosen from nonionic hydrophilic monomers present in an amount ranging from 3% to 92% by weight relative to the total weight of the at least one block.

35. The linear ethylenic block copolymer according to claim 1, wherein the at least one additional monomer is chosen from hydrophobic monomers present in an amount ranging from 0 to 98% by weight relative to the total weight of the at least one block.

36. The linear ethylenic block copolymer according to claim 35, wherein the at least one additional monomer is chosen from hydrophobic monomers present in an amount ranging from 3% to 92% by weight relative to the total weight of the at least one block.

37. The linear ethylenic block copolymer according to claim 1, wherein the ethylenic hydrocarbon containing 2 to 10 carbons is chosen from ethylene, isoprene, and butadiene.

38. The linear ethylenic block copolymer according to claim 1, wherein in the (meth)acrylates of formula:

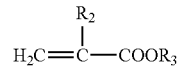

$R_3$ is chosen from isobornyl, phenyl, 2-phneylethyl, t-butylbenzyl, benzyl, furfurylmethyl, tetrahydrofurfurylmethyl, and $(OC_3H_6)_m$—OH groups, wherein m ranges from 5 to 300.

39. The linear ethylenic block copolymer according to claim 1, wherein in the (meth)acrylamides of formula:

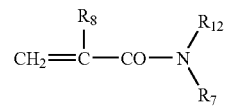

$R_7$ and $R_{12}$, which may be identical or different, are chosen isobornyl, phenyl, 2-phneylethyl, t-butylbenzyl, benzyl, furfurylmethyl, tetrahydrofurfurylmethyl, and $(OC_3H_6)_m$—OH groups, wherein m ranges from 5 to 300.

40. The linear ethylenic block copolymer according to claim 1, wherein in the vinyl compounds of formula $CH_2$=$CH$—$R_9$, $R_9$ is chosen from isobornyl, cyclohexane, phenyl, 2-phenylethyl, benzyl, N-vinylpyrrolidone, N-vinylcaprolactam, furfurylmethyl, and tetrahydrofurfurylmethyl groups.

41. The linear ethylenic block copolymer according to claim 1, wherein the at least one additional monomer is selected from the group consisting of:
hydroxyalkyl (meth)acrylates and (meth)acrylamides, wherein the alkyl group contains 2 to 4 carbon atoms;
$(C_{1-4}$alkoxy$(C_{1-4}$alkyl (meth)acrylates and (meth)acrylamides;
(meth)acrylamide and, N,N-dimethylacrylamide;
(meth)acrylates and (meth)acrylamides containing a group —$(OC_2H_4)_m$—OR", wherein m ranges from 5 to 300 and R" is chosen from hydrogen atoms and C1-C4 alkyl radicals;
vinyllactams;
vinyl ethers;
vinylacetamide, N-vinylpyrrolidone and N-vinyl-caprolactam; and
polysaccharide (meth)acrylates.

42. The linear ethylenic block copolymer according to claim 41, wherein:
the hydroxyalkyl (meth)acrylates and (meth)acrylamides are selected from the group consisting of 2-hydroxyethyl acrylate, 2-hydroxyethyl methacrylate, 2-hydroxy-propyl methacrylate, 4-hydroxybutyl methacrylate and N-(2-hydroxypropyl) (meth) acrylamide;
the $(C_{1-4}$alkoxy$(C_{1-4})$alkyl (meth)acrylates and (meth)acrylamides are selected from the group consisting of methoxyethyl, 2-ethoxyethyl, methoxypropyl and bis (2-ethoxyethyl) (meth)acrylates and (meth) acrylamides;
the (meth)acrylates and (meth)acrylamides containing a group —$(OC_2H_4)_m$—OR" are selected from the group consisting of polyethylene glycol (meth)acrylates and (meth)acrylamides containing a methoxy or hydroxyl end group;
the vinyllactams are selected from the group consisting of vinylpyrrolidone and vinylcaprolactam;
the vinyl ethers are selected from the group consisting of methyl vinyl ether and ethyl vinyl ether; and the polysaccharide (meth)acrylates are selected from the group consisting of sucrose acrylate and ethylglucoside (meth)acrylate.

43. The linear ethylenic block copolymer according to claim 1, wherein the at least one additional monomer is selected from the group consisting of:
t-butylbenzyl acrylate, t-butylcyclohexyl acrylate, isobornyl acrylate, furfuryl acrylate, n-hexyl acrylate, t-butyl acrylate, cyclohexyl acrylate, hydroxyethyl acrylate, methyl acrylate, ethyl acrylate, isobutyl acrylate, methoxyethyl acrylate, n-butyl acrylate, ethyihexyl acrylate, hexyl acrylate, octyl acrylate, lauryl acrylate, isooctyl acrylate, and isodecyl acrylate;
t-butylbenzyl methacrylate, t-butylcyclohexyl methacrylate, isobornyl methacrylate, methyl methacrylate, cyclohexyl methacrylate, ethyl methacrylate, benzyl methacrylate, isobutyl methacrylate, butyl methacrylate, n-hexyl methacrylate, ethyihexyl methacrylate, octyl methacrylate, lauryl methacrylate, isooctyl methacrylate, and isodecyl methacrylate;
styrene, vinylcyclohexane, vinyl acetate, methyl vinyl ether, vinyl neononanoate, and vinyl neododecanoate; and
N-butylacrylamide, N-isopropytacrylamide, N,N-dimethylacrylamide, N,N-dibutylacrylamide, N-t-butylacrylamide, and N-octylacrylamide.

44. The linear ethylenic block copolymer according to claim 1, comprising at least one block comprising monomers chosen from n-hexyl methacrylate, ethyl acrylate, isobutyl acrylate, n-butyl acrylate, ethylhexyl acrylate; methoxy poly(ethylene glycol) monomethacrylate with a number m of ethylene glycol units of 8,12, 90, 180 or 200; methoxy poly(ethylene glycol) monomethacrylamide with m=8,12, 90, 180 or 200; poly(ethylene glycol)OH (meth)acrylate with m=8, 12, 90, 180 or 200; poly(ethylene glycol)OH (meth)acrylamide with m=8, 12, 90, 180 or 200; vinylpyrrolidone, vinylcaprolactam; methyl vinyl ether and ethyl vinyl ether.

45. The linear ethylenic block copolymer according to claim 1, wherein the copolymer is a diblock copolymer chosen from:
poly(acrylic acid-co-butyl acrylate)-b-poly(methyl methacrylate-co-acrylic acid), and
poly(methacrylic acid-co-butyl acrylate)-b-poly(methyl methacrylate-co-methacrylic acid).

46. The linear ethylenic block copolymer according to claim 1, wherein the copolymer is a triblock copolymer chosen from:
poly(methyl methacrylate-co-acrylic acid)-b-poly(acrylic acid-co-butyl acrylate)-b-poly(methyl methacrylate-co-acrylic acid),
poly(methyl methacrylate-co-(meth)acrylic acid)-b-poly(methacrylic acid-co-butyl acrylate)-b-poly(methyl methacrylate-co-methacrylic acid),
poly(methyl acrylate-co-acrylic acid)-b-poly-(acrylic acid-co-butyl acrylate)-b-poly(methyl acrylate-co-acrylic acid),
poly(acrylic acid-co-butyl acrylate)-b-poly(methyl methacrylate-co-acrylic acid)-b-poly(acrylic acid-co-butyl acrylate);
poly(acrylic acid)-b-poly(acrylic acid-co-butyl acrylate)-b-poly(acrylic acid);
poly(methacrylic acid)-b-poly(methacrylic acid-co-butyl acrylate)-b-poly(methacrylic acid);
poly(acrylic acid-co-cyclohexyl acrylate)-b-poly(acrylic acid-co-butyl acrylate)-b-poly(acrylic acid-co-cyclohexyl acrylate);
poly(acrylic acid-co-butyl acrylate)-b-poly(acrylic acid-co-cyclohexyl acrylate)-b-poly(acrylic acid-co-butyl acrylate);
poly(acrylic acid-co-cyclohexyl methacrylate)-b-poly(acrylic acid-co-butyl acrylate)-b-poly(acrylic acid-co-cyclohexyl methacrylate);
poly(acrylic acid-co-isobornyl acrylate)-b-poly(acrylic acid-co-butyl acrylate)-b-poly(acrylic acid-co-isobornyl acrylate);
poly(methyl methacrylate-co-acrylic acid )-b-poly(acrylic acid-co-methoxypoly(ethylene glycol)monomethacrylate comprising 12 ethylene glycol units)-b-poly(methyl methacrylate-co-acrylic acid); and
poly(acrylic acid-co-methoxypoly(ethylene glycol) monomethacrylate comprising 12 ethylene glycol units)-b-poly(methyl methacrylate-co-acrylic acid)-b-poly(acrylic acid-co-methoxypoly(ethylene glycol) monomethacrylate comprising 12 ethylene glycol units).

47. The linear ethylenic block copolymer according to claim 1, wherein at least one of the blocks of the copolymer has a glass transition temperature (Tg) of less than or equal to 20° C.

48. The linear ethylenic block copolymer according to claim 1, wherein at least one of the blocks of the copolymer has a glass transition temperature (Tg) of greater than or equal to 20° C.

49. The linear ethylenic block copolymer according to claim 1, wherein the copolymer, in a solution comprising the copolymer at a concentration of 20% by weight in water, has a viscosity at 25°0 C. ranging from 1 to 10,000 mPa·s.

50. The linear ethylenic block copolymer according to claim 49, wherein the copolymer, in a solution comprising the copolymer at a concentration of 20% by weight in water, has a viscosity at 25° C. ranging from 5 to 3000 mPa·s.

51. The linear ethylenic block copolymer according to claim 1, wherein the copolymer is soluble or dispersible in water, at 25° C., to a proportion of 5% by weight.

* * * * *

UNITED STATES PATENT AND TRADEMARK OFFICE
CERTIFICATE OF CORRECTION

PATENT NO. : 7,632,905 B2  Page 1 of 1
APPLICATION NO. : 11/101648
DATED : December 15, 2009
INVENTOR(S) : Boupat et al.

It is certified that error appears in the above-identified patent and that said Letters Patent is hereby corrected as shown below:

In claim 1, column 31, line 57, "C4- to 12-membered" should read --4- to 12-membered--.

In claim 1, column 32, line 58, "CH2=CH-CH2-R9and" should read --CH2=CH-CH2-R9 and--.

In claim 15, column 34, line 26, "vinyiphosphonic" should read --vinylphosphonic--.

In claim 30, column 37, lines 28-29, "N,N-dimethyl-N-(2-meth-acryloyloxyethyl)-N-(3-sulfopropyI)" should read --N,N-dimethyl-N-(2-meth-acryloyloxyethyl)-N-(3-sulfopropyl)--.

In claim 38, column 38, line 7, "2-phneylethyl," should read --2-phenylethyl,--.

In claim 39, column 38, lines 19-20, "chosen isobornyl," should read --chosen from isobornyl,--.

In claim 38, column 38, line 20, "2-phneylethyl," should read --2-phenylethyl,--.

In claim 41, column 38, line 35, "(C1-4alkoxy(Cl-4alkyl" should read --(C1-4)alkoxy(C1-4)alkyl--.

In claim 41, column 38, line 37, "and," should read --and--.

In claim 42, column 38, line 54, "(C1-4alkoxy(C1-4)alkyl" should read --(C1-4)alkoxy(C1-4)alkyl--.

In claim 43, column 39, line 11, "ethyihexyl" should read --ethylhexyl--.

In claim 43, column 39, line 18, "ethyihexyl" should read --ethylhexyl--.

In claim 43, column 39, line 24, "N-isopropytacrylamide," should read --N-isopropylacrylamide,--.

In claim 44, column 39, line 33, "m=8,12," should read --m=8, 12,--.

In claim 49, column 40, line 44, "25°0 C." should read --25° C.--.

Signed and Sealed this

Twenty-third Day of February, 2010

David J. Kappos
*Director of the United States Patent and Trademark Office*